(12) United States Patent
Lee et al.

(10) Patent No.: US 10,512,437 B2
(45) Date of Patent: Dec. 24, 2019

(54) TOMOGRAPHY APPARATUS AND METHOD OF RECONSTRUCTING TOMOGRAPHY IMAGE THEREOF

(71) Applicant: SAMSUNG ELECTRONICS CO., LTD., Suwon-si (KR)

(72) Inventors: Kyoung-yong Lee, Hwaseong-si (KR); Sangnam Nam, Suwon-si (KR); Duhgoon Lee, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 274 days.

(21) Appl. No.: 15/517,270

(22) PCT Filed: Sep. 21, 2015

(86) PCT No.: PCT/KR2015/009852
§ 371 (c)(1),
(2) Date: Apr. 6, 2017

(87) PCT Pub. No.: WO2016/076525
PCT Pub. Date: May 19, 2016

(65) Prior Publication Data
US 2017/0303868 A1    Oct. 26, 2017

(30) Foreign Application Priority Data
Nov. 14, 2014   (KR) .................. 10-2014-0159182

(51) Int. Cl.
| | |
|---|---|
| *A61B 6/03* | (2006.01) |
| *A61B 6/02* | (2006.01) |
| *A61B 6/00* | (2006.01) |
| *G06T 11/00* | (2006.01) |
| *G06T 7/00* | (2017.01) |

(52) U.S. Cl.
CPC ............. *A61B 6/032* (2013.01); *A61B 6/027* (2013.01); *A61B 6/4085* (2013.01);
(Continued)

(58) Field of Classification Search
CPC .. A61B 6/00; A61B 6/03; A61B 6/032; A61B 6/02; A61B 6/5288; A61B 6/4085;
(Continued)

(56) References Cited

U.S. PATENT DOCUMENTS

| | | | |
|---|---|---|---|
| 7,203,272 B2 | 4/2007 | Chen | |
| 7,678,063 B2 | 3/2010 | Felmlee et al. | |

(Continued)

FOREIGN PATENT DOCUMENTS

| | | |
|---|---|---|
| JP | 2004-254773 A | 9/2004 |
| KR | 10-2009-0078513 A | 7/2009 |

OTHER PUBLICATIONS

Communication dated Nov. 7, 2017 by the European Patent Office in counterpart European Patent Application No. 15858221.3.
(Continued)

*Primary Examiner* — Jurie Yun
(74) *Attorney, Agent, or Firm* — Sughrue Mion, PLLC

(57) ABSTRACT

A tomography apparatus that may reduce partial scan artifacts includes: a data acquirer configured to acquire tomography data when X-rays are emitted as a cone beam to an object while rotating by one cycle angular section that is less than one rotation; and an image reconstructor configured to reconstruct a tomography image by using corrected tomography data that is obtained by applying to the tomography data a weight that is set based on at least one of a view that is included in the one cycle angular section and a cone angle in the cone beam.

20 Claims, 14 Drawing Sheets

(52) U.S. Cl.
CPC .......... *A61B 6/5205* (2013.01); *A61B 6/5258* (2013.01); *A61B 6/5288* (2013.01); *G06T 7/0012* (2013.01); *G06T 11/006* (2013.01); *G06T 2207/10081* (2013.01); *G06T 2211/421* (2013.01); *G06T 2211/436* (2013.01)

(58) Field of Classification Search
CPC ..... A61B 6/027; A61B 6/5258; A61B 6/5205; G06T 7/00; G06T 7/0012; G06T 11/00; G06T 11/006; G06T 11/003; G06T 2207/10081; G06T 2211/421; G06T 2211/40
USPC .......................... 378/4, 19, 21, 901; 382/131
See application file for complete search history.

(56) References Cited

U.S. PATENT DOCUMENTS

| | | | |
|---|---|---|---|
| 7,751,524 | B2 | 7/2010 | Horiuchi et al. |
| 8,284,892 | B2 | 10/2012 | Pack et al. |
| 8,630,474 | B2 | 1/2014 | Dennerlein et al. |
| 2006/0262893 | A1 | 11/2006 | Tang et al. |
| 2008/0273780 | A1 | 11/2008 | Kohlmyer et al. |
| 2009/0028288 | A1 | 1/2009 | Horiuchi et al. |
| 2012/0207370 | A1 | 8/2012 | Fahimian et al. |
| 2013/0251229 | A1 | 9/2013 | Ramirez Giraldo et al. |
| 2014/0016847 | A1 | 1/2014 | Nett et al. |

OTHER PUBLICATIONS

Pack, et al., "Mitigating cone-beam artifacts in short-scan CT imaging for large cone-angle scans", 12th International Meeting on Fully Three-Dimensional Image Reconstruction in Radiology and Nuclear Medicine, Jun. 16, 2013, pp. 300-303.

Written Opinion dated Jan. 14, 2016, issued by the International Searching Authority in counterpart International Patent Application No. PCT/KR2015/009852 (PCT/ISA/237).

Search Report dated Jan. 14, 2016, issued by the International Searching Authority in counterpart International Patent Application No. PCT/KR2015/009852 (PCT/ISA/210).

[Fig. 1A]
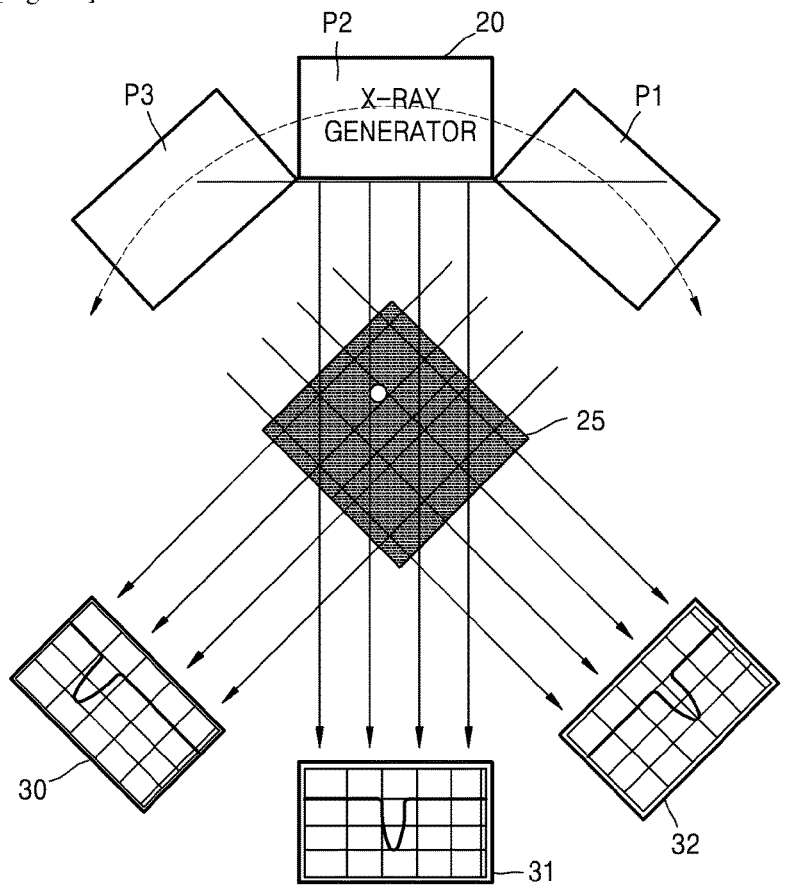
[Fig. 1B]
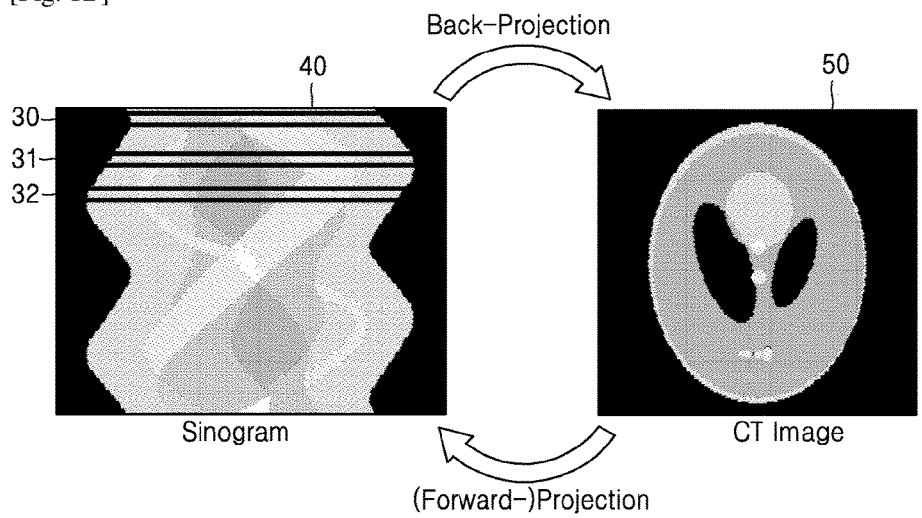

[Fig. 2]
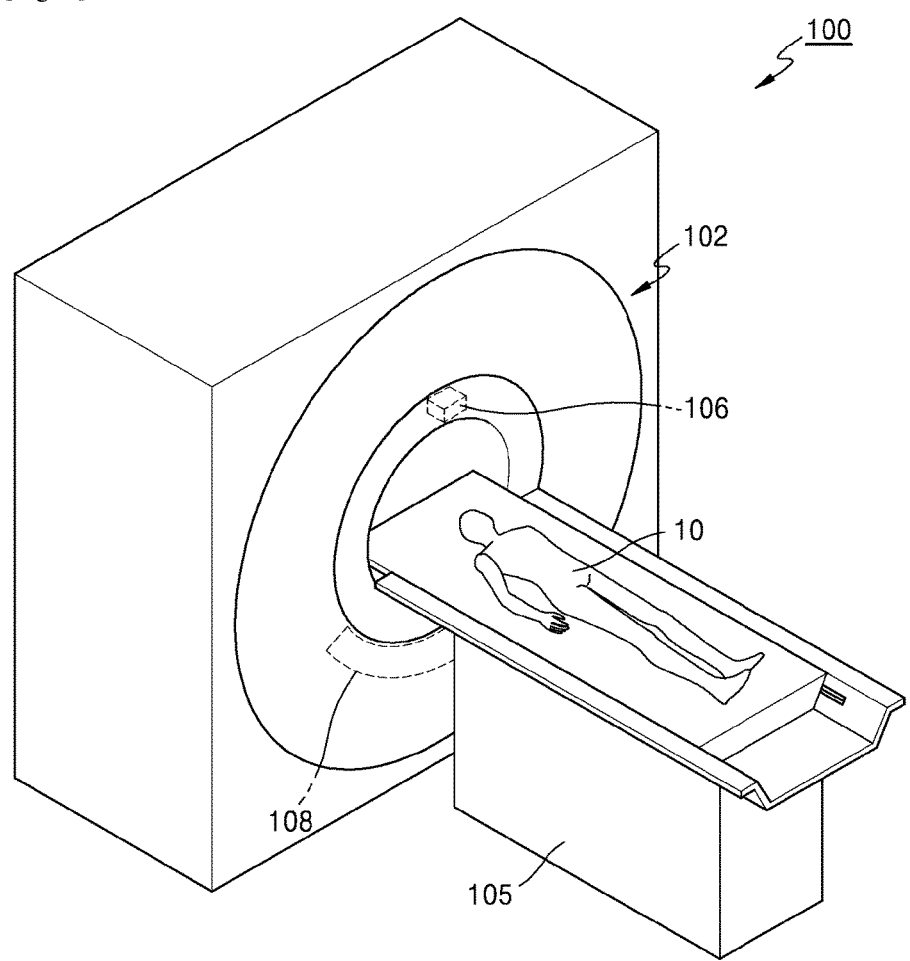

[Fig. 3]
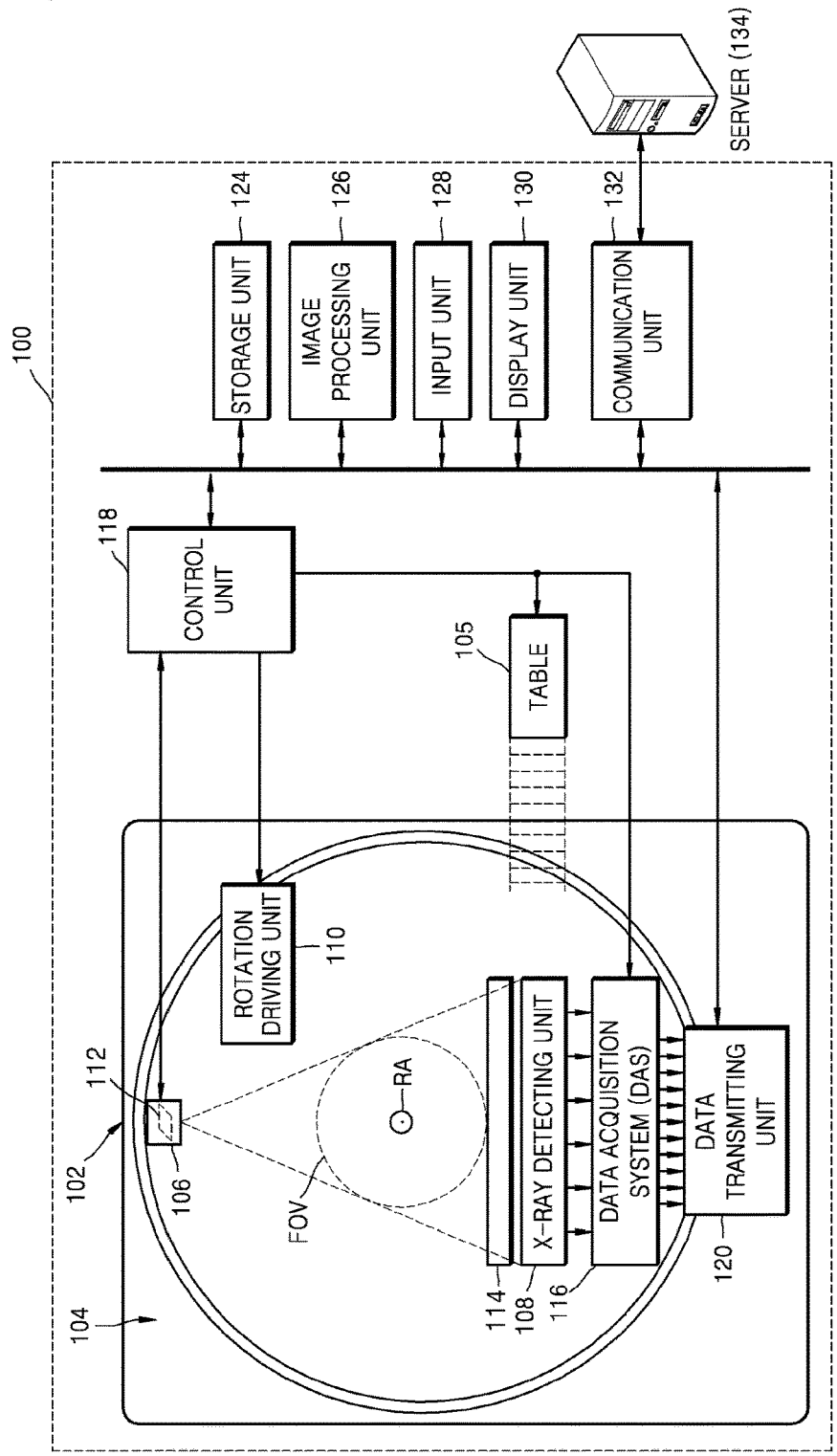

[Fig. 4]
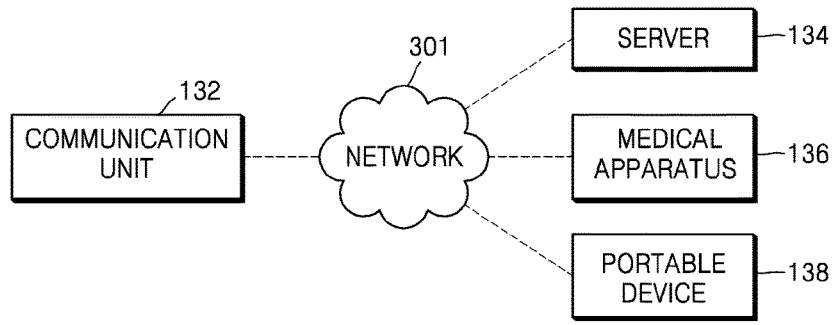
[Fig. 5A]
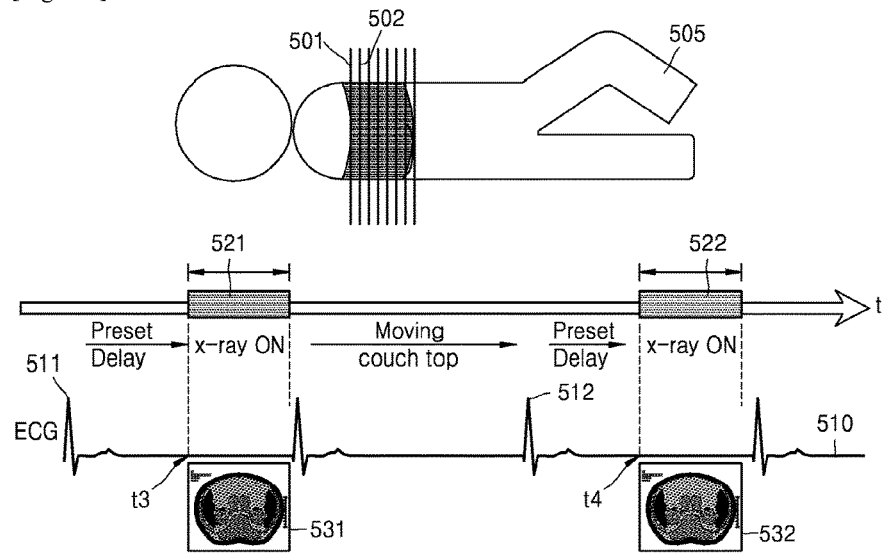
[Fig. 5B]
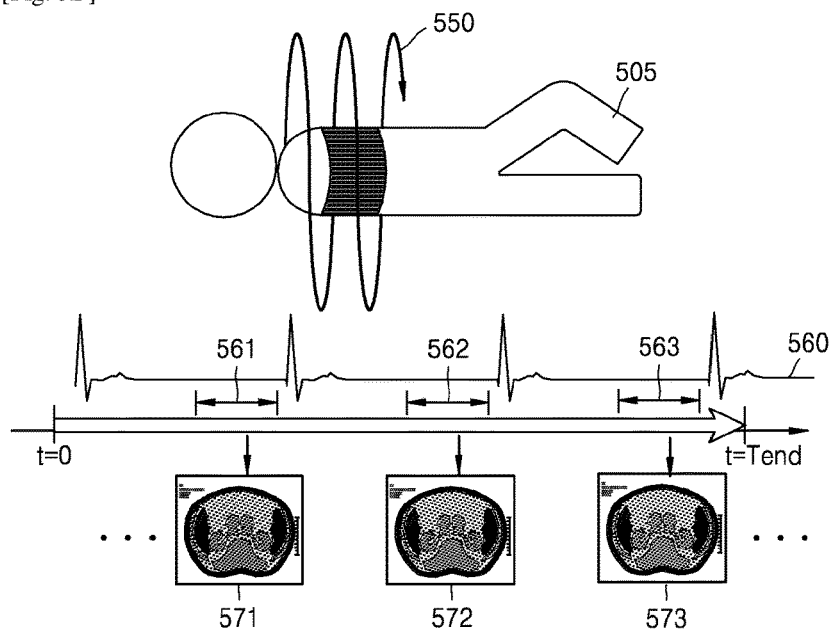

[Fig. 6]
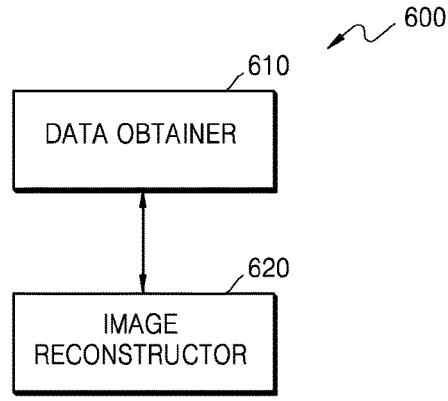
[Fig. 7]
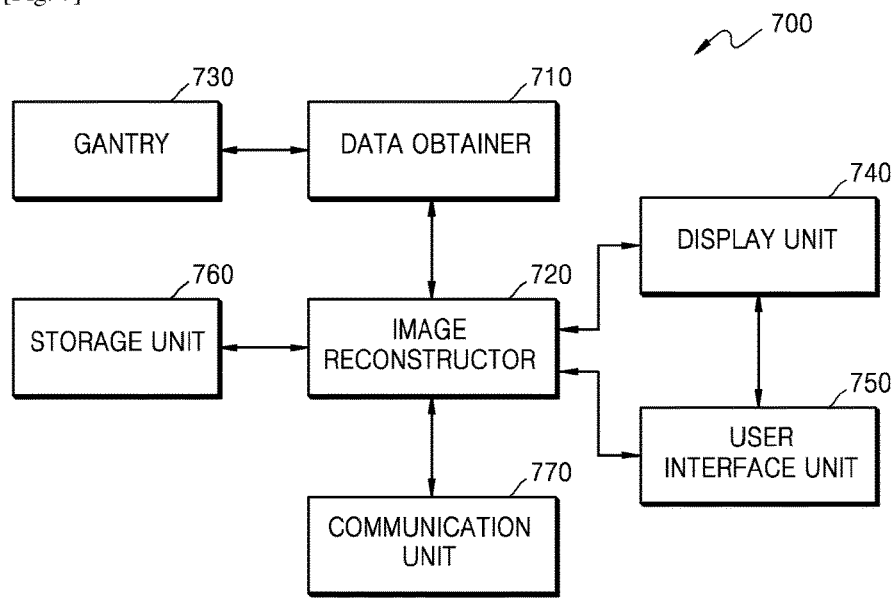
[Fig. 8A]
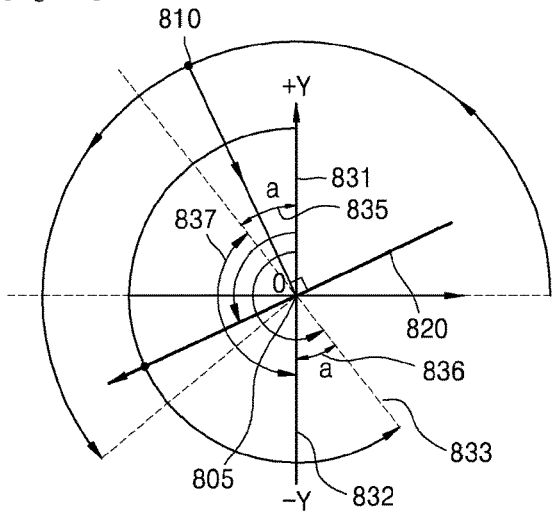

[Fig. 8B]
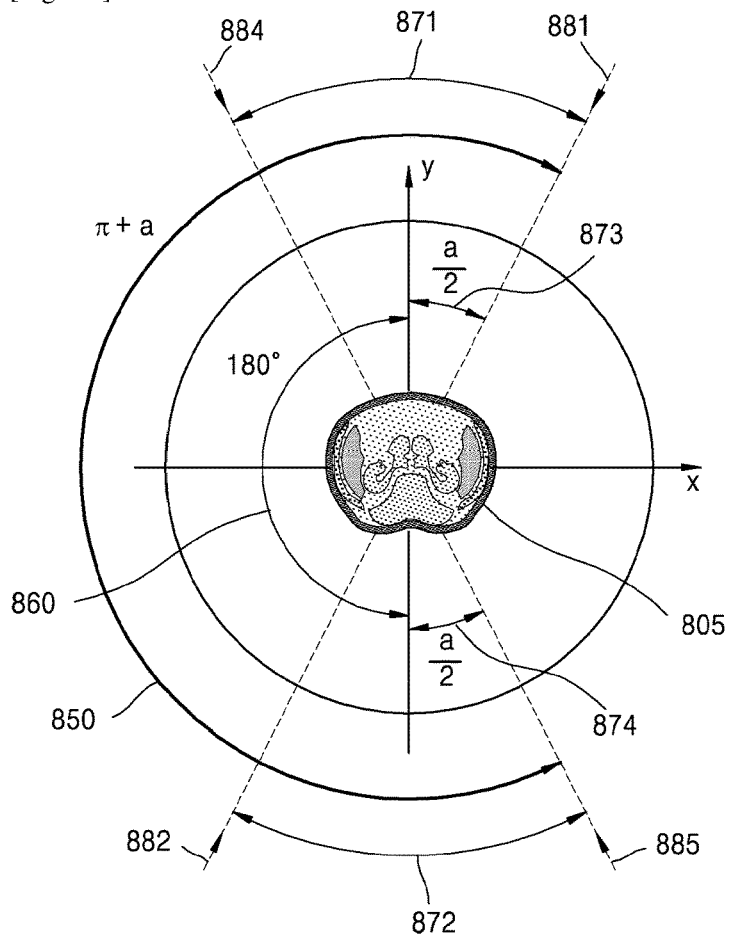
[Fig. 9]
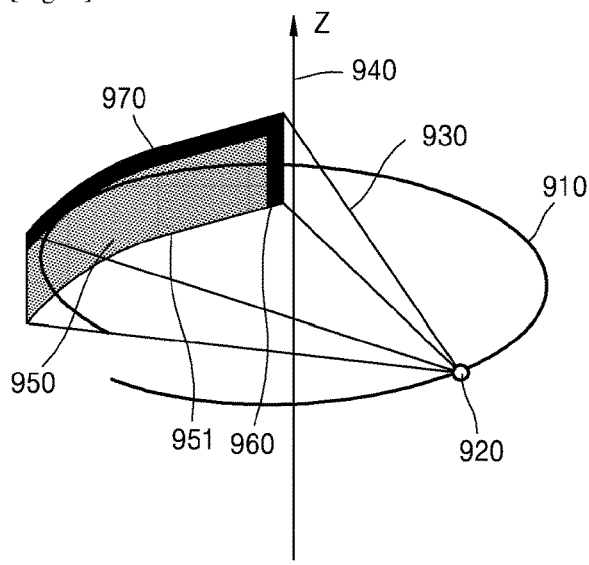

[Fig. 10A]
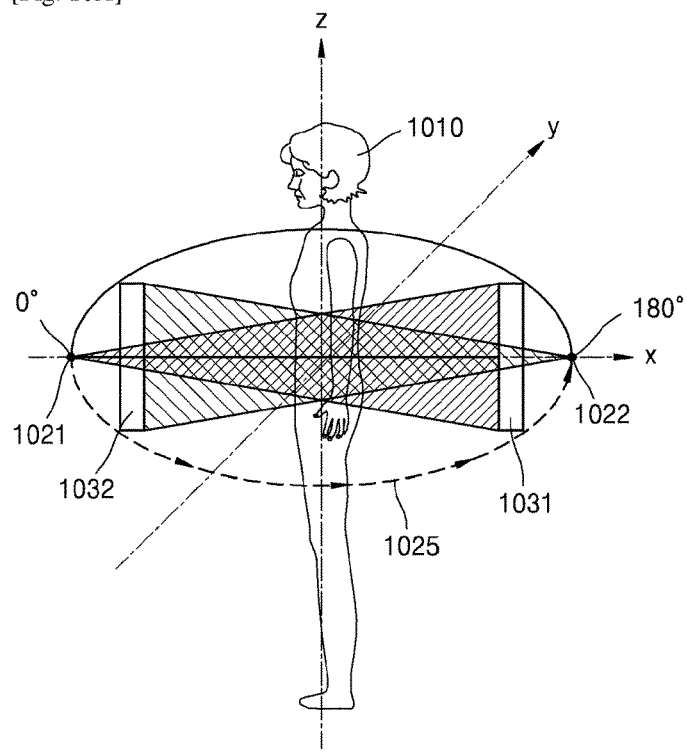
[Fig. 10B]
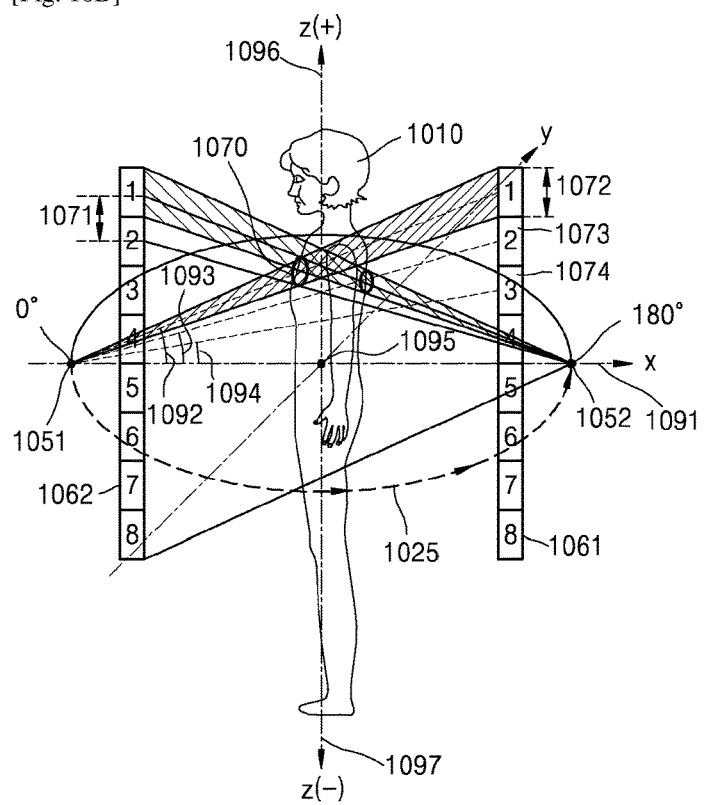

[Fig. 11A]
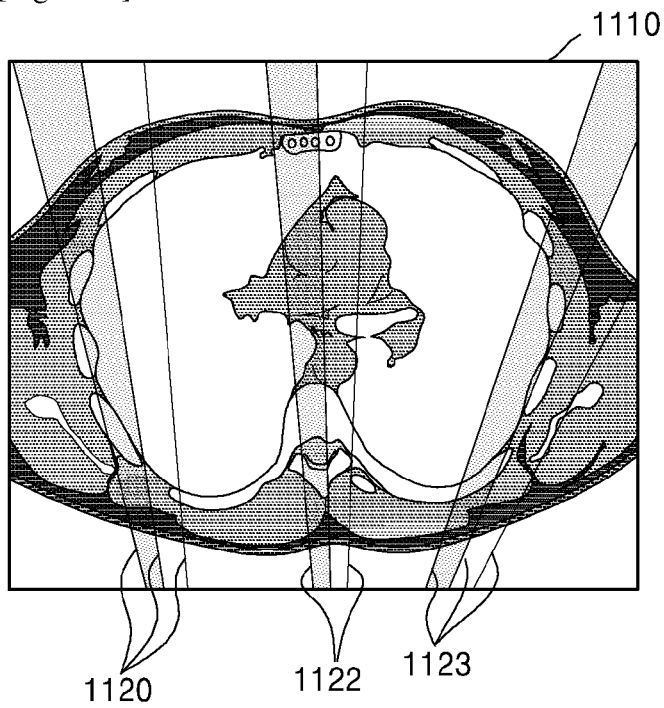
[Fig. 11B]
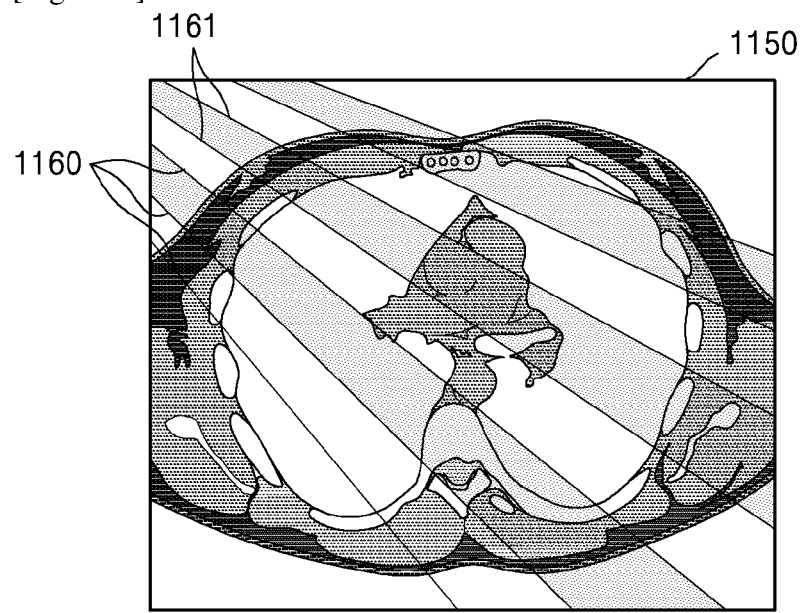

[Fig. 12]
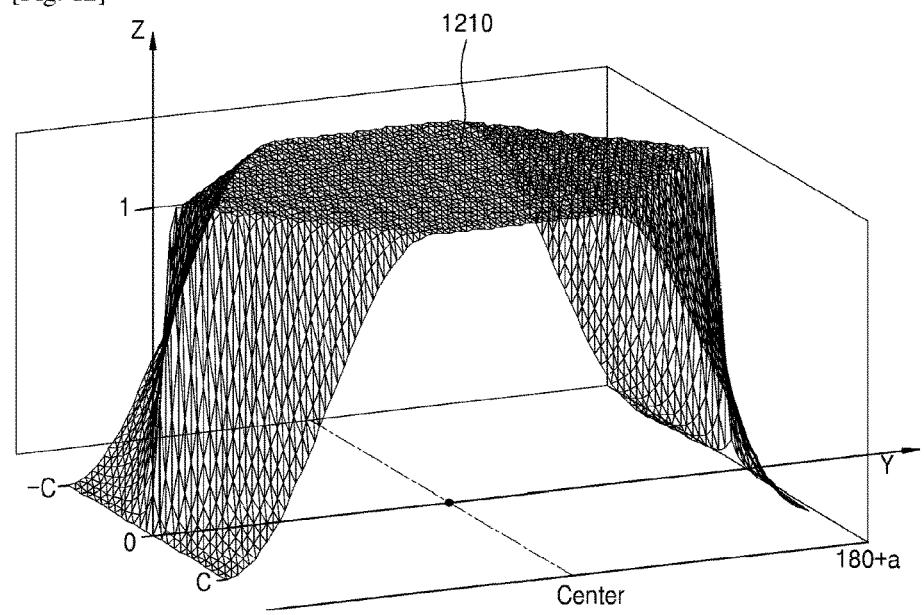
[Fig. 13A]
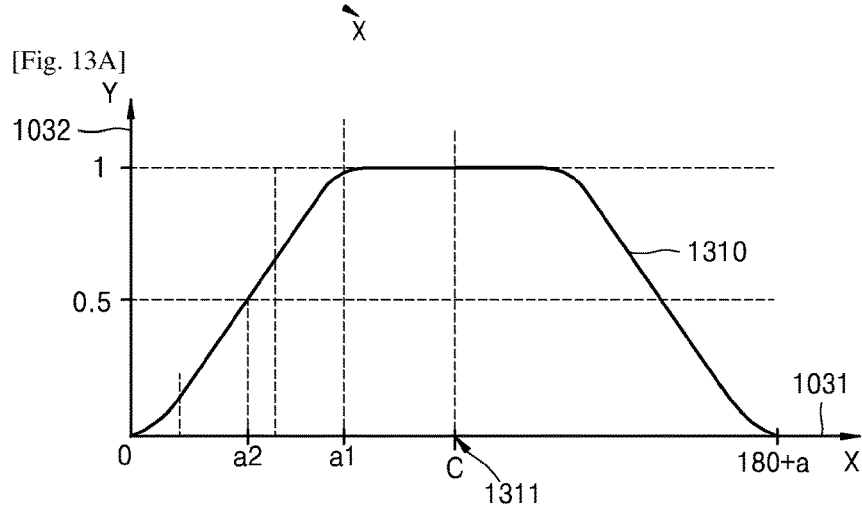
[Fig. 13B]
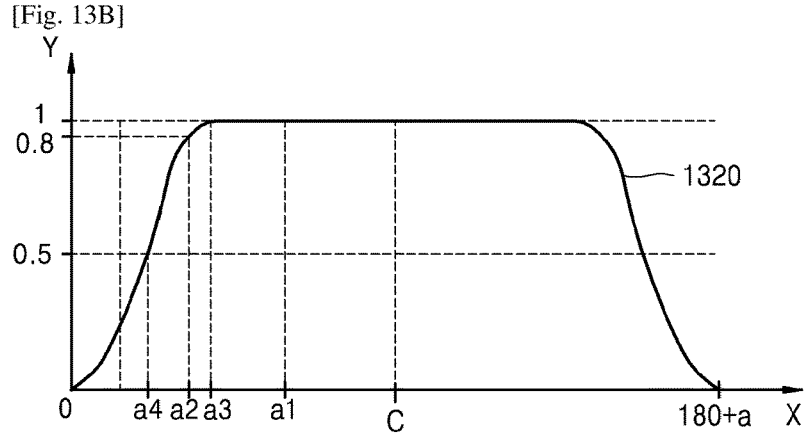

[Fig. 13C]
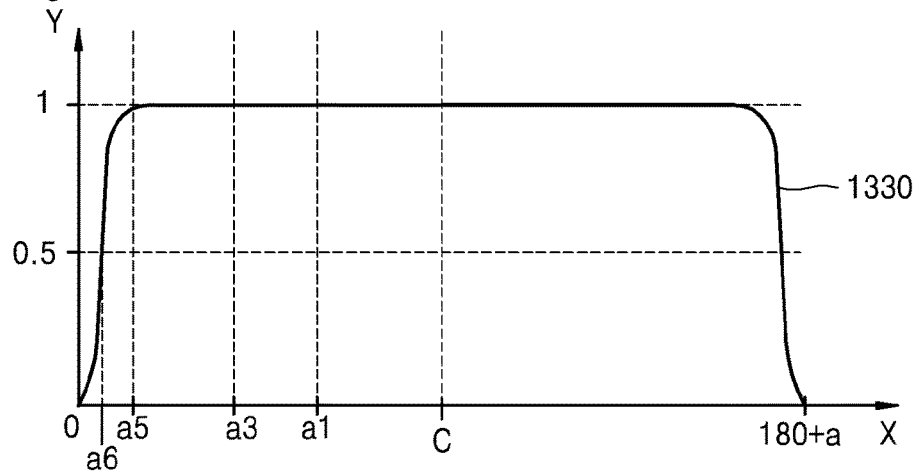
[Fig. 14A]
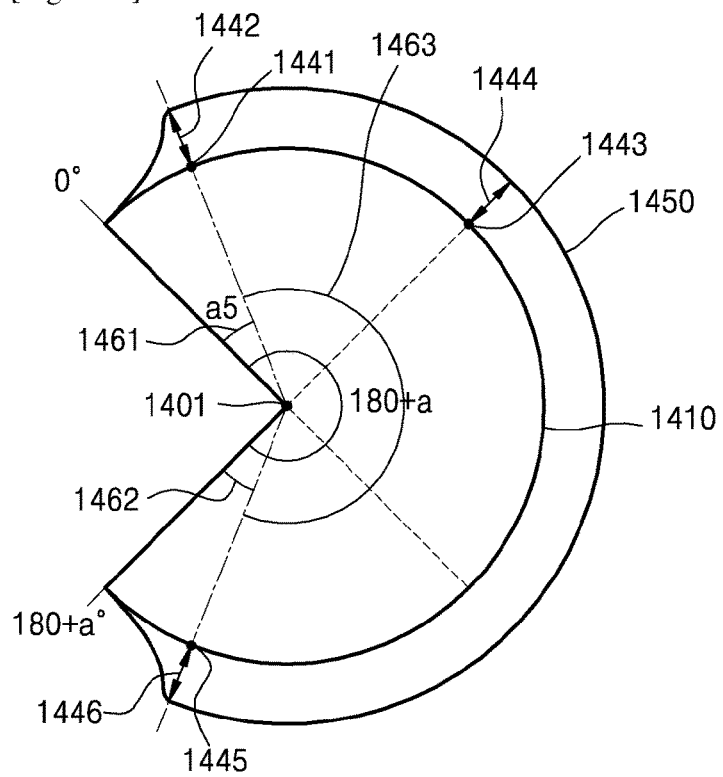

[Fig. 14B]
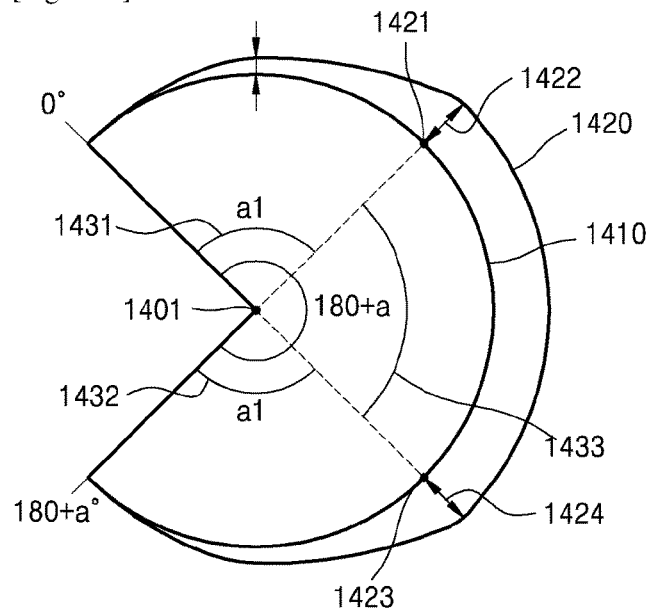
[Fig. 15A]
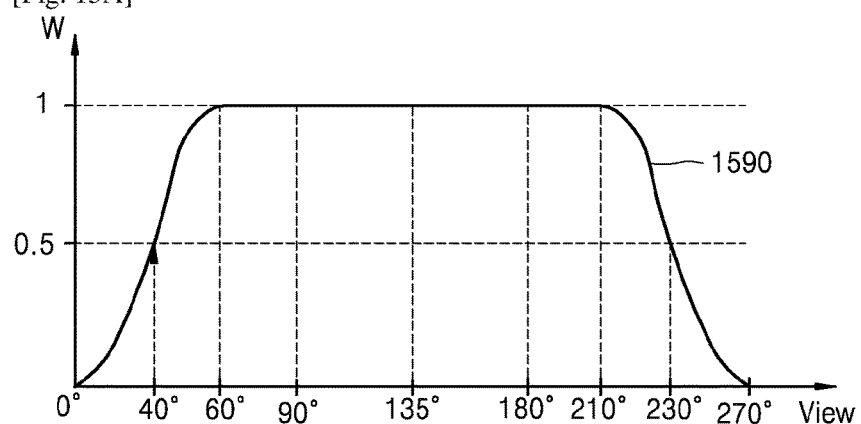

[Fig. 15B]
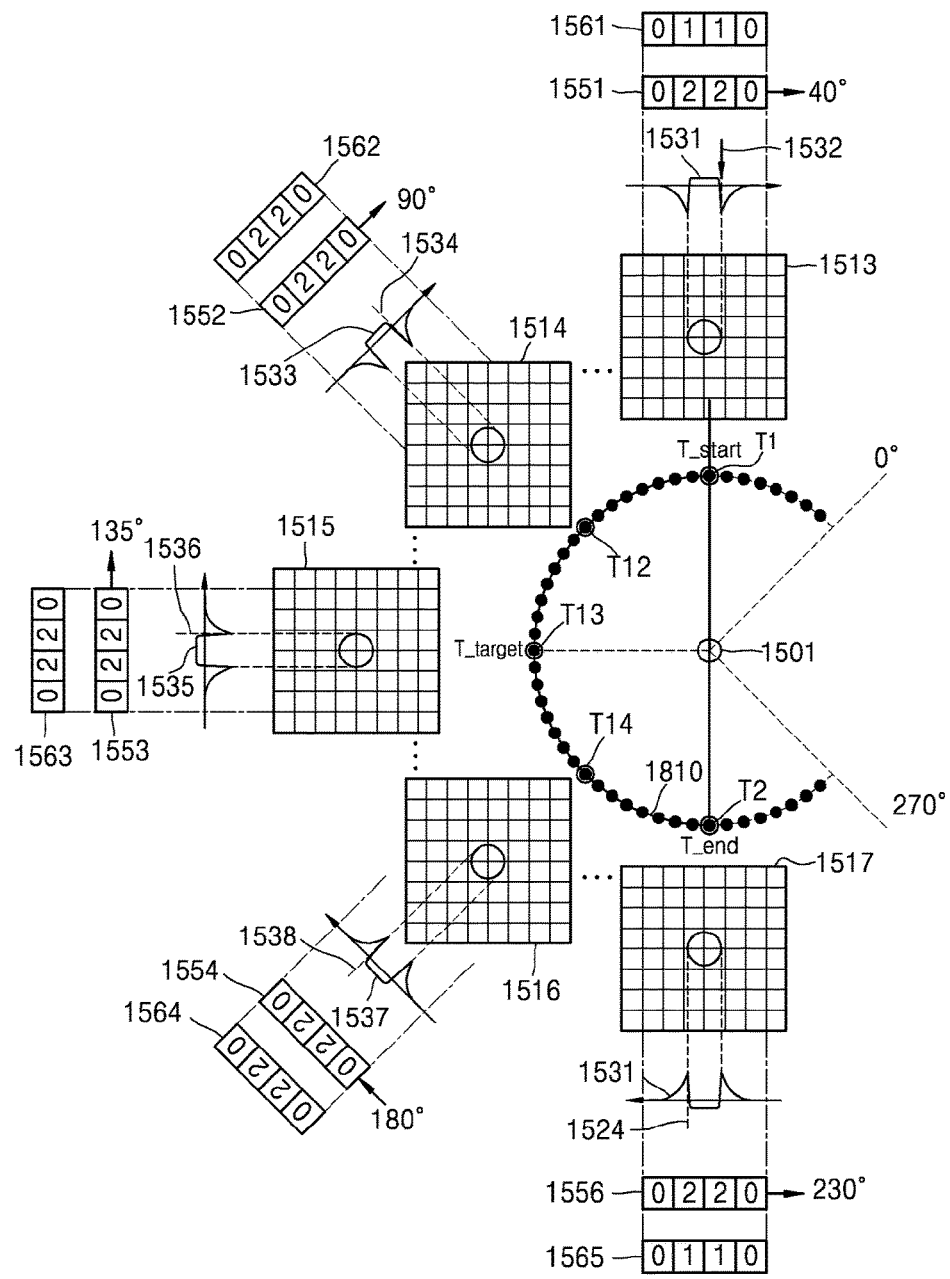

[Fig. 16A]
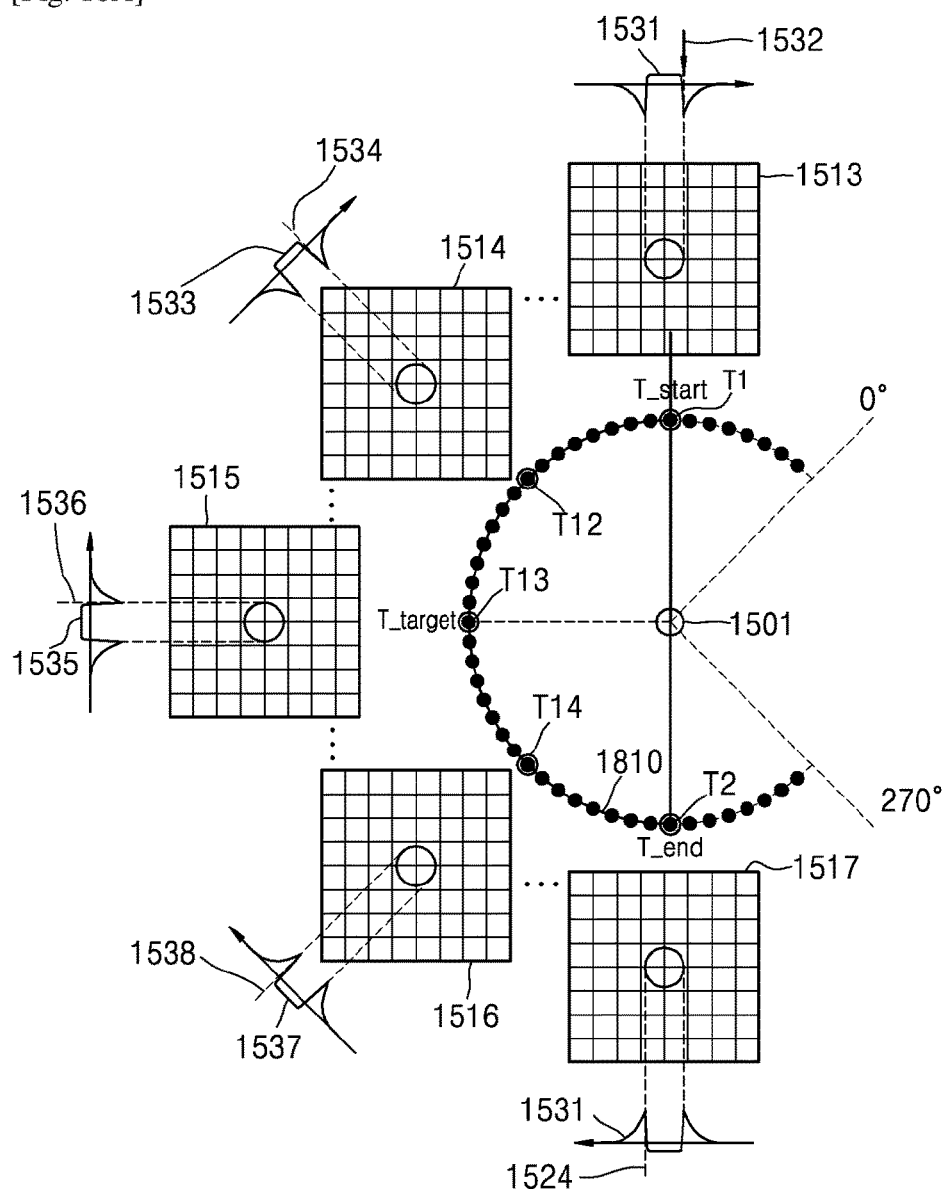

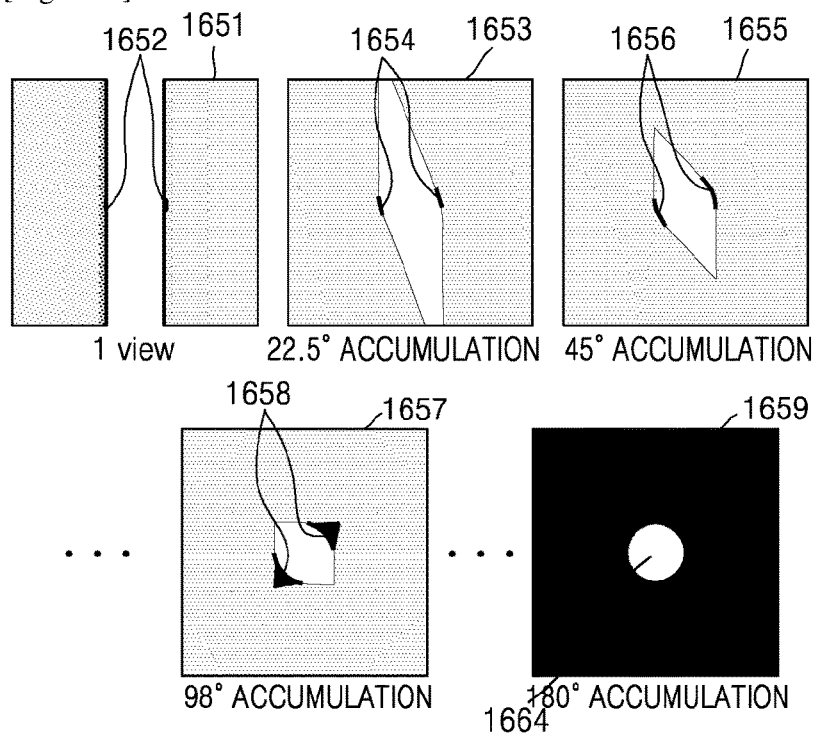
[Fig. 16B]
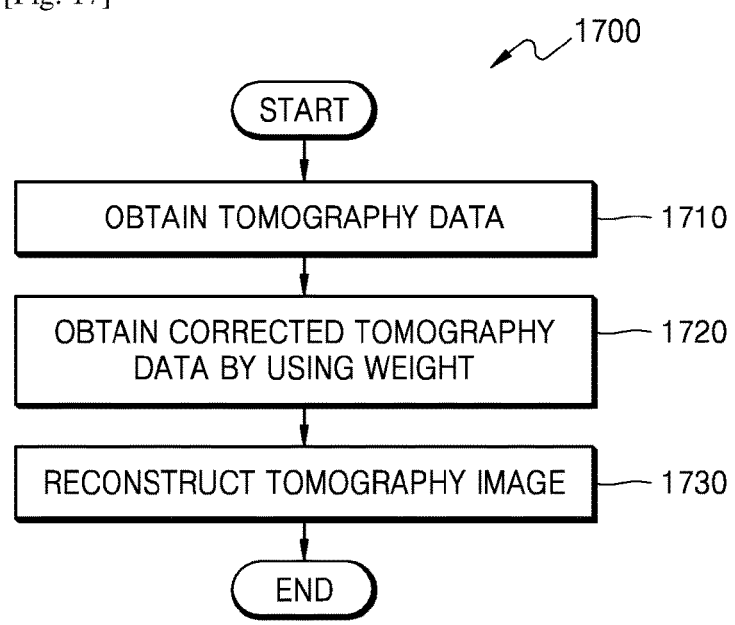
[Fig. 17]

TOMOGRAPHY APPARATUS AND METHOD OF RECONSTRUCTING TOMOGRAPHY IMAGE THEREOF

TECHNICAL FIELD

One or more exemplary embodiments relate to a tomography apparatus and a method of reconstructing a tomography image thereof.

BACKGROUND ART

A medical imaging apparatus is an apparatus for acquiring an image of an inner structure of an object. A medical imaging apparatus noninvasively images and processes structural details, tissue, and the flow of a fluid in a patient's body to be examined and displays a result of the imaging and processing to a user. The user, for example, a doctor, may check the patient's health condition and may diagnose the patient's disease by using a medical image that is output by the medical imaging apparatus.

A computed tomography (CT) apparatus is a representative apparatus for imaging an object by emitting X-rays to a patient.

Since a CT apparatus that is a tomography apparatus among medical imaging apparatuses may provide a cross-sectional image of an object and may display an inner structure (e.g., organs such as kidneys and lungs) of the object without an overlap therebetween, unlike a general X-ray imaging apparatus, the CT apparatus is widely used to precisely diagnose a disease. Hereinafter, a medical image that is obtained by a tomography apparatus is referred to as a tomography image and a medical image that is obtained by a CT apparatus is referred to as a CT image.

In order to obtain a tomography image, tomography imaging is performed on an object by using a tomography apparatus to obtain raw data. A tomography image is reconstructed by using the obtained raw data. The raw data may be projection data that is obtained by projecting X-rays to the object or a sinogram that is a set of projection data.

For example, in order to obtain a tomography image, an operation of reconstructing an image has to be performed by using a sinogram that is obtained through tomography imaging. An operation of reconstructing the tomography image will now be explained with reference to FIGS. 1A and 1B.

FIGS. 1A and 1B are views for explaining CT imaging and reconstruction.

In detail, FIG. 1A is a view for explaining an operation performed by a CT apparatus to perform CT imaging by rotating about an object 25 and obtain raw data. FIG. 1B is a view for explaining a sinogram and a reconstructed CT image that are obtained by the CT imaging.

The CT apparatus generates X-rays, emits the X-rays to the object 25, and detects the X-rays that pass through the object 25 by using an X-ray detector (not shown). The X-ray detector generates raw data corresponding to the detected X-rays.

In detail, referring to FIG. 1A, an X-ray generator 20 that is included in the CT apparatus emits X-rays to the object 25. During CT imaging, the X-ray generator 20 rotates about the object 25 and acquires a plurality of pieces of raw data, e.g., first through third raw data 30, 31, and 32, corresponding to rotation angles by which the X-ray generator 20 rotates. In detail, the first raw data 30 is obtained by detecting X-rays that are applied to the object 20 from a position P1 and the second raw data 31 is obtained by detecting X-rays that are applied to the object 25 from a position P2. Also, the third raw data 32 is obtained by detecting X-rays that are applied to the object 25 from a position P3. Each of the first raw data 30, the second raw data 31, and the third raw data 32 may be projection data that is obtained by emitting X-rays to the object 25 from one view.

In order to obtain one cross-sectional CT image, the X-ray generator 20 has to perform CT imaging by rotating by at least 180°.

Referring to FIG. 1B, one sinogram 40 may be obtained by combining a plurality of pieces of projection data, e.g., the first through third raw data 30, 31, and 32 together, obtained by moving the X-ray generator 20 by predetermined angular sections, as described above with reference to FIG. 1A. The sinogram 40 is a sinogram obtained by the X-ray generator 20 that performs CT imaging by rotating by one cycle. The sinogram 40 corresponding to the rotation of one cycle may be used to generate one cross-sectional CT image. The rotation of one cycle may be equal to or greater than a half-turn or one turn according to a specification of a CT system.

A CT image 50 is reconstructed by performing filtered back-projection on the sinogram 40.

Various artifacts may occur in the reconstructed CT image 50. The various artifacts in the CT image 50 may reduce the quality of the CT image 50, thereby reducing the accuracy with which a user, e.g., a doctor, reads the CT image 50 and diagnoses a disease.

Accordingly, it is very important to reconstruct the CT image 50 with reduced artifacts.

DISCLOSURE

Technical Solution

One or more exemplary embodiments include a tomography apparatus that may reduce artifacts that may occur in a reconstructed tomography image and a method of reconstructing a tomography image.

One or more exemplary embodiments include a tomography apparatus that may reduce partial scan artifacts that may occur when a tomography image is reconstructed by using a half-reconstruction method and a method of reconstructing a tomography image.

Advantageous Effects

According to exemplary embodiments, a tomography apparatus and a method of reconstructing a tomography image thereof may effectively reduce partial scan artifacts.

DESCRIPTION OF DRAWINGS

FIGS. 1A and 1B are views for explaining computed tomography (CT) imaging and reconstruction;

FIG. 2 is a perspective view of a CT system;

FIG. 3 is a block diagram illustrating a structure of the CT system according to an exemplary embodiment;

FIG. 4 is a block diagram for explaining communication performed by a communication unit;

FIGS. 5A and 5B are views for explaining a scan mode used in tomography imaging;

FIG. 6 is a block diagram of a tomography apparatus according to an exemplary embodiment;

FIG. 7 is a block diagram of a tomography apparatus according to another exemplary embodiment;

FIGS. 8A and 8B are views for explaining reconstruction of a tomography image according to half-reconstruction;

FIG. 9 is a view for explaining a beam of X-rays emitted to an object;

FIGS. 10A and 10B are views for explaining an operation of performing tomography imaging by emitting a cone beam to an object;

FIGS. 11A and 11B are views for explaining partial scan artifacts that occur in a reconstructed tomography image;

FIG. 12 is a view for explaining a weight used in tomography image reconstruction according to an exemplary embodiment;

FIGS. 13A through 13C are views for explaining a weight used in tomography image reconstruction according to another exemplary embodiment;

FIGS. 14A and 14B are views for explaining a weight used in tomography image reconstruction according to another exemplary embodiment;

FIGS. 15A and 15B are views for explaining an operation of reconstructing a tomography image according to an exemplary embodiment;

FIGS. 16A and 16B are views for explaining an operation of reconstructing a tomography image according to another exemplary embodiment; and FIG. 17 is a flowchart of a method of reconstructing a tomography image according to an exemplary embodiment.

BEST MODE

One or more exemplary embodiments include a tomography apparatus that may reduce artifacts that may occur in a reconstructed tomography image and a method of reconstructing a tomography image.

One or more exemplary embodiments include a tomography apparatus that may reduce partial scan artifacts that may occur when a tomography image is reconstructed by using a half-reconstruction method and a method of reconstructing a tomography image.

Additional aspects will be set forth in part in the description which follows and, in part, will be apparent from the description, or may be learned by practice of the presented exemplary embodiments.

According to one or more exemplary embodiments, a tomography apparatus includes: a data acquirer configured to acquire tomography data when X-rays are emitted as a cone beam to an object while rotating by one cycle angular section that is less than one rotation; and an image reconstructor configured to reconstruct a tomography image by using corrected tomography data that is acquired by applying to the tomography data a weight that is set based on at least one of a view that is included in the one cycle angular section and a cone angle in the cone beam.

The image reconstructor may compensate for artifacts that occur due to a difference between data in a first view that is included in the one cycle angular section and data in a second view that faces the first view in the tomography data, by using the weight.

The image reconstructor may acquire the corrected tomography data by applying the weight to the tomography data corresponding to at least one view that is included in the one cycle angular section in order to compensate for the difference.

The image reconstructor may acquire the corrected tomography data by multiplying the weight by the tomography data.

The image reconstructor may set the weight that as the cone angle increases and as the weight corresponds to a view value farther away from a center of the one cycle angular section, the weight decreases.

The weight may be set based on the view and the cone angle, and may decrease as the weight corresponds to a view value farther away from a center of the one cycle angular section and as an absolute value of the cone angle increases.

The weight may be set based on the view, and may decrease as the weight corresponds to a view value farther away from a center of the one cycle angular section.

The weight may be set based on the cone angle, and may decrease as the cone angle increases.

The weight may be set to a value that is inversely proportional to a difference between data in a first view that is included in the one cycle angular section and a second view that faces the first view, in the tomography data corresponding to a predetermined cone angle.

When a detector array detects X-rays that pass through the object, the weight may be set based on a position of a slice of the detector array corresponding to the cone angle.

When the tomography data includes a plurality of pieces of projection data corresponding to a plurality of views that are included in the one cycle angular section, the image reconstructor may reconstruct the tomography image by performing back-projection or filtered back-projection on a plurality of pieces of corrected projection data that are acquired by applying the weight to each of the plurality of pieces of projection data.

The image reconstructor may set the weight so that a value of the weight applied to at least one projection data acquired in at least one view corresponding to a central interval of the one cycle angular section is greater than a value of the weight applied to at least one projection data acquired in at least one view corresponding to an interval other than the central interval.

The one cycle angular section may have a value that is equal to or greater than 180° and less than 360°, wherein the tomography data includes a plurality of pieces of projection data corresponding to a plurality of views that are included in the one cycle angular section.

The image reconstructor may reconstruct a plurality of tomography images corresponding to a plurality of slices by using the corrected tomography data, wherein noise characteristics of the plurality of tomography images are different from one another.

When the cone beam is emitted to the object while rotating by the one cycle angular section, the data acquirer may acquire the tomography data that is used to reconstruct multi-slice images.

According to one or more exemplary embodiments, a method of reconstructing a tomography image includes: when X-rays that are emitted as a cone beam to an object while rotating by one cycle angular section that is less than one rotation, acquiring tomography data; acquiring a weight based on at least one of a view that is included in the one cycle angular section and a cone angle in the cone beam; and reconstructing a tomography image by using corrected tomography data that is acquired by applying the weight to the tomography data.

The reconstructing of the tomography image may further include reconstructing the tomography image by compensating for artifacts that occur due to a difference between data in a first view that is included in the one cycle angular section and data in a second view that faces the first view in the tomography data by using the weight.

The reconstructing of the tomography image may include acquiring the corrected tomography data by applying the weight to the tomography data corresponding to at least one view that is included in the one cycle angular section in order to compensate for the difference.

The reconstructing of the tomography image may include acquiring the corrected tomography data by multiplying the weight by the tomography data.

The acquiring of the weight may include setting the weight that as the cone angle increases and as the weight corresponds to a view value farther away from a center of the one cycle angular section, the weight decreases.

The weight may be set based on the view and the cone angle, and may decrease as the weight corresponds to a view value farther away from a center of the one cycle angular section and as an absolute value of the cone angle increases.

The weight may be set based on the view, and may decrease as the weight corresponds to a view value farther away from a center of the one cycle angular section.

The weight may be set based on the cone angle, and may decrease as the cone angle increases.

The weight may be set to a value that is inversely proportional to a difference between data in a first view that is included in the one cycle angular section and a second view that faces the first view, in the tomography data corresponding to a predetermined cone angle.

When a detector array detects X-rays that pass through the object, the weight may be set based on a position of a slice of the detector array corresponding to the cone angle.

The reconstructing of the tomography image may include, when the tomography image includes a plurality of pieces of projection data corresponding to a plurality of views that are included in the one cycle angular section, reconstructing the tomography image by performing back-projection or filtered back-projection on a plurality of pieces of corrected projection data that are acquired by applying the weight, which is set according to each of the plurality of views, to each of the plurality of pieces of projection data.

The acquiring of the weight may include setting the weight so that a value of the weight applied to at least one projection data acquired in at least one view corresponding to a central interval of the one cycle angular section is greater than a value of the weight applied to at least one projection data acquired in at least one view corresponding to a interval other than the central interval.

The one cycle angular section may have a value that is equal to or greater than 180° and less than 360°, wherein the tomography data includes a plurality of pieces of projection data corresponding to a plurality of views that are included in the one cycle angular section.

The reconstructing of the tomography image may include reconstructing a plurality of tomography images corresponding to a plurality of slices by using the corrected tomography data, wherein noise characteristics of the plurality of tomography images are different from one another.

When the cone beam is emitted to the object while rotating by the one cycle angular section, the acquiring of the tomography data may include acquiring the tomography data that is used to reconstruct multi-slice images.

MODE FOR INVENTION

Advantages and features of one or more embodiments of the inventive concept and methods of accomplishing the same may be understood more readily by reference to the following detailed description of the embodiments and the accompanying drawings. In this regard, the present embodiments may have different forms and should not be construed as being limited to the descriptions set forth herein. Rather, these embodiments are provided so that this disclosure will be thorough and complete and will fully convey the concept of the present embodiments to one of ordinary skill in the art, and the inventive concept will only be defined by the appended claims. Like reference numerals refer to like elements throughout the specification.

Hereinafter, the terms used in the specification will be briefly defined, and the embodiments will be described in detail.

All terms including descriptive or technical terms which are used herein should be construed as having meanings that are obvious to one of ordinary skill in the art. However, the terms may have different meanings according to the intention of one of ordinary skill in the art, precedent cases, or the appearance of new technologies. Also, some terms may be arbitrarily selected by the applicant, and in this case, the meaning of the selected terms will be described in detail in the detailed description of the inventive concept. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term "unit" in the embodiments of the inventive concept means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Reference will now be made in detail to embodiments, examples of which are illustrated in the accompanying drawings. In this regard, the present embodiments may have different forms and should not be construed as being limited to the descriptions set forth herein. In the following description, well-known functions or constructions are not described in detail so as not to obscure the embodiments with unnecessary detail.

Throughout the specification, an "image" may mean multi-dimensional data formed of discrete image elements, e.g., pixels in a two-dimensional (2D) image and voxels in a three-dimensional (3D) image. For example, the image may include a medical image of an object which is captured by a computed tomography (CT) apparatus.

Throughout the specification, a "CT image" may mean an image generated by synthesizing a plurality of X-ray images that are obtained by photographing an object while a CT apparatus rotates around at least one axis with respect to the object.

Throughout the specification, an "object" may be a human, an animal, or a portion of a human or animal. For example, the object may be an organ (e.g., the liver, heart, womb, brain, breast, or abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to the physical body.

Throughout the specification, a "user" may be, but is not limited to, a medical expert including a medical doctor, a nurse, a medical laboratory technologist, a medical image expert, or a technician who repairs a medical apparatus.

Since a tomography system, such as a CT system, is capable of providing a cross-sectional image of an object, the tomography system may display an inner structure (e.g., organs such as kidneys, lungs, etc.) of the object without an overlap therebetween, contrary to a general X-ray imaging apparatus.

In detail, examples of the tomography system may include tomography apparatuses such as a CT apparatus, an optical coherence tomography (OCT) apparatus, and a position emission tomography (PET)-CT apparatus.

The following will be explained on the assumption that a tomography system is a CT system.

The CT system may obtain a plurality of pieces of image data with a thickness not more than 2 mm several hundred times per second and then may process the plurality of pieces of image data, so that the CT system may provide a relatively accurate cross-sectional image of the object. According to the related art, only a horizontal cross-sectional image of the object can be obtained, but this issue has been overcome due to various image reconstruction methods. Examples of 3D image reconstruction methods are as below:

Shade surface display (SSD)—an initial 3D imaging method of displaying only voxels having a predetermined Hounsfield Units (HU) value.

Maximum intensity projection (MIP)/minimum intensity projection (MinIP)—a 3D imaging method of displaying only voxels having the greatest or smallest HU value from among voxels that construct an image.

Volume rendering (VR)—an imaging method capable of adjusting a color and transmittance of voxels that constitute an image, according to areas of interest.

Virtual endoscopy ? a method that allows endoscopy observation in a 3D image that is reconstructed by using the VR method or the SSD method.

Multi-planar reformation (MPR) ? a method of reconstructing an image into a different cross-sectional image. A user may reconstruct an image in any desired direction.

Editing ? a method of editing adjacent voxels so as to allow a user to easily observe an area of interest in volume rendering.

Voxel of interest (VOI) ? a method of displaying only a selected area in volume rendering.

A CT system 100 according to an embodiment of the inventive concept will now be described with reference to FIG. 2. The CT system 100 may include various types of devices.

FIG. 2 schematically illustrates the CT system 100. Referring to FIG. 2, the CT system 100 may include a gantry 102, a table 105, an X-ray generator 106, and an X-ray detector 108.

The gantry 102 may include the X-ray generator 106 and the X-ray detector 108.

An object 10 may be positioned on the table 105.

The table 105 may move in a predetermined direction (e.g., at least one of up, down, right, and left directions) during CT imaging. Also, the table 105 may tilt or rotate by a predetermined angle in a predetermined direction.

The gantry 102 may also tilt by a predetermined angle in a predetermined direction.

FIG. 3 is a block diagram illustrating a structure of the CT system 100.

The CT system 100 may include the gantry 102, the table 105, a control unit 118, a storage unit 124, an image processing unit 126, an input unit 128, a display unit 130, and a communication unit 132.

As described above, the object 10 may be positioned on the table 105. In the present embodiment, the table 105 may move in a predetermined direction (e.g., at least one of up, down, right, and left directions), and movement of the table 105 may be controlled by the control unit 118.

The gantry 102 may include a rotating frame 104, the X-ray generator 106, the X-ray detector 108, a rotation driving unit 110, a data acquisition system (DAS) 116, and a data transmitting unit 120.

The gantry 102 may include the rotating frame 104 having a loop shape capable of rotating with respect to a predetermined rotation axis RA. Also, the rotating frame 104 may have a disc shape.

The rotating frame 104 may include the X-ray generator 106 and the X-ray detector 108 that are arranged to face each other so as to have predetermined fields of view FOV. The rotating frame 104 may also include an anti-scatter grid 114. The anti-scatter grid 114 may be positioned between the X-ray generator 106 and the X-ray detector 108.

In detail, one X-ray generator 106 is one X-ray source. For example, when the rotating frame 104 includes two X-ray generators 106, it may be stated that the rotating frame 104 includes a dual source. When the rotating frame 104 includes one X-ray generator 106, the one X-ray generator 106 that is included in the rotating frame 104 may be referred to as a 'single source' and when the rotating frame 104 includes two X-ray generators (not shown), the two X-ray generators that are included in the rotating frame 104 may be referred to as a 'dual source'. Also, among the two X-ray generators that form the dual source, one X-ray generator may be referred to as a first source and the other X-ray generator may be referred to as a second source. Also, the CT system 100 may be referred to as a 'single source tomography apparatus' when one X-ray generator is included in the rotating frame 104 and the CT system 100 may be referred to as a 'dual source tomography apparatus' when two X-ray generators are included in the rotating frame 104.

In a medical imaging system, X-ray radiation that reaches a detector (or a photosensitive film) includes not only attenuated primary radiation that forms a valuable image but also scattered radiation that deteriorates the quality of an image. In order to transmit most of the primary radiation and to attenuate the scattered radiation, the anti-scatter grid 114 may be positioned between a patient and the detector (or the photosensitive film).

For example, the anti-scatter grid 114 may be formed by alternately stacking lead foil strips and an interspace material such as a solid polymer material, solid polymer, or a fiber composite material. However, formation of the anti-scatter grid 114 is not limited thereto.

The rotating frame 104 may receive a driving signal from the rotation driving unit 80 and may rotate the X-ray generator 106 and the X-ray detector 108 at a predetermined rotation speed. The rotating frame 104 may receive the driving signal and power from the rotation driving unit 110 while the rotating frame 104 contacts the rotation driving unit 110 via a slip ring (not shown). Also, the rotating frame 104 may receive the driving signal and power from the rotation driving unit 110 via wireless communication.

The X-ray generator 106 may receive a voltage and current from a power distribution unit (PDU) (not shown) via a slip ring (not shown) and a high voltage generating unit (not shown), and may generate and emit X-rays. When the high voltage generating unit applies a predetermined voltage (hereinafter, referred to as a tube voltage) to the X-ray generator 106, the X-ray generator 106 may generate X-rays having a plurality of energy spectra that correspond to the tube voltage.

The X-rays generated by the X-ray generator 106 may be emitted in a predetermined form due to a collimator 112.

The X-ray detector 108 may be positioned to face the X-ray generator 106. The X-ray detector 108 may be positioned to face the X-ray generator 106. Each of the plurality of X-ray detecting devices may establish one channel but one or more embodiments of the inventive concept are not limited thereto. Also, the X-ray detector 108 may include a one-dimensional (1D) detector array or a 2D detector array.

The X-ray detector 108 may detect the X-rays that are generated by the X-ray generator 106 and that are transmitted through the object 10, and may generate an electrical signal corresponding to intensity of the detected X-rays.

The X-ray detector 108 may include an indirect-type X-ray detector for detecting radiation after converting the radiation into light, and a direct-type X-ray detector for detecting radiation after directly converting the radiation into electric charges. The indirect-type X-ray detector may use a scintillator. Also, the direct-type X-ray detector may use a photon counting detector. The DAS 116 may be connected to the X-ray detector 108. Electrical signals generated by the X-ray detector 108 may be acquired by the DAS 116. Electrical signals generated by the X-ray detector 108 may be acquired by wire or wirelessly by the DAS 116. Also, the electrical signals generated by the X-ray detector 108 may be provided to an analog-to-digital converter (not shown) via an amplifier (not shown).

According to a slice thickness or the number of slices, only some of a plurality of pieces of data collected by the X-ray detector 108 may be provided to the image processing unit 126 via the data transmitting unit 120, or the image processing unit 126 may select only some of the plurality of pieces of data.

Such a digital signal may be provided to the image processing unit 126 via the data transmitting unit 120. The digital signal may be provided to the image processing unit 126 by wire or wirelessly.

The control unit 118 may control an operation of each of the elements in the CT system 100. For example, the control unit 118 may control operations of the table 105, the rotation driving unit 110, the collimator 112, the DAS 116, the storage unit 124, the image processing unit 126, the input unit 128, the display unit 130, the communication unit 132, or the like.

The image processing unit 126 may receive data acquired by the DAS 116 (e.g., pure data that is data before processing), via the data transmitting unit 120, and may perform pre-processing.

The pre-processing may include, for example, a process of correcting a sensitivity irregularity between channels and a process of correcting signal loss due to a rapid decrease in signal strength or due to the presence of an X-ray absorbing material such as metal.

Data output by the image processing unit 126 may be referred to as raw data or projection data. The projection data may be stored in the storage unit 124 with imaging conditions (e.g., the tube voltage, an imaging angle, etc.) during the acquisition of data.

The projection data may be a group of data values that correspond to the intensity of the X-rays that have passed through the object 10. For convenience of description, a group of a plurality of pieces of projection data that are simultaneously obtained from all channels at the same imaging angle is referred to as a projection data set.

The storage unit 124 may include at least one storage medium from among a flash memory-type storage medium, a hard disk-type storage medium, a multimedia card micro-type storage medium, card-type memories (e.g., an SD card, an XD memory, and the like), random access memory (RAM), static random access memory (SRAM), read-only memory (ROM), electrically erasable programmable ROM (EEPROM), programmable ROM (PROM), magnetic memory, a magnetic disc, and an optical disc.

The image processing unit 126 may reconstruct a cross-sectional image of the object 10 by using the acquired projection data set. The cross-sectional image may be a 3D image. In other words, the image processing unit 126 may reconstruct a 3D image of the object 10 by using a cone beam reconstruction method or the like, based on the acquired projection data set.

The input unit 128 may receive an external input with respect to an X-ray tomography imaging condition, an image processing condition, or the like. For example, the X-ray tomography imaging condition may include tube voltages, an energy value setting with respect to a plurality of X-rays, a selection of an imaging protocol, a selection of an image reconstruction method, a setting of a FOV area, the number of slices, a slice thickness, a parameter setting with respect to image post-processing, or the like. Also, the image processing condition may include a resolution of an image, an attenuation coefficient setting for the image, setting for an image combining ratio, or the like.

The input unit 128 may include a device for receiving a predetermined input from an external source. For example, the input unit 128 may include a microphone, a keyboard, a mouse, a joystick, a touch pad, a touch pen, a voice recognition device, a gesture recognition device, or the like.

The display unit 130 may display an X-ray image reconstructed by the image processing unit 126.

Exchanges of data, power, or the like between the aforementioned elements may be performed by using at least one of wired communication, wireless communication, and optical communication.

The communication unit 132 may perform communication with an external device, an external medical apparatus, etc. via a server 134 or the like. The communication will now be described with reference to FIG. 4.

FIG. 4 is a block diagram for explaining communication performed by the communication unit 132.

The communication unit 132 may be wiredly or wirelessly connected to a network 301 and therefore may communicate with the server 134, a medical apparatus 136, or a portable device 138. The communication unit 132 may exchange data with a hospital server or other medical apparatuses in a hospital connected via a picture archiving and communication system (PACS).

Also, the communication unit 132 may perform data communication with the portable device 138 or the like, according to the digital imaging and communications in medicine (DICOM) standard.

The communication unit 132 may transmit and receive data related to diagnosing the object 10, via the network 301. Also, the communication unit 132 may transmit and receive a medical image obtained from the medical apparatus 136 such as a magnetic resonance imaging (MRI) apparatus, an X-ray apparatus, or the like.

Furthermore, the communication unit 132 may receive a diagnosis history or a medical treatment schedule about a patient from the server 134 and may use the diagnosis history or the medical treatment schedule to diagnose the patient. Also, the communication unit 132 may perform data communication not only with the server 134 or the medical apparatus 136 in a hospital but also with the portable device 138 of a user or patient.

Also, the communication unit 132 may transmit information about a device error, information about a quality control status, or the like to a system manager or a service manager via the network 301, and may receive a feedback regarding the information from the system manager or service manager.

Also, the CT system 100 may perform tomography imaging according to various scan modes. The various scan modes used during tomography imaging may include a prospective mode and a retrospective mode, which will be explained below in detail with reference to FIG. 5. Also, tomography apparatuses 600 and 700 according to exemplary embodiments which will be described below with reference to FIGS. 6 through 16 may perform tomography imaging according to various scan methods. The various scan methods used during tomography imaging may include an axial scan method and a helical scan method, which will be explained below in detail with reference to FIG. 5.

Also, the CT system 100 may reconstruct a tomography image according to a half-reconstruction method or a full reconstruction method.

A method of reconstructing one tomography image by using raw data that is acquired when the X-ray generator 106 rotates by an interval that is equal to or greater than a half-turn and less than one turn is referred to as a half-reconstruction method and a method of reconstructing one tomography image by using raw data acquired when the X-ray generator 106 rotates by one turn is referred to as a full reconstruction method. Also, a time for which or an angle (or a phase) by which the X-ray generator 106 rotates in order to obtain raw data that is necessary to reconstruct one tomography image is referred to as 'one cycle'. Also, 'one cycle angular section' may refer to an angular section by which the X-ray generator 106 rotates in order to obtain raw data necessary to reconstruct one tomography image. Also, the 'one cycle angular section' may refer to an interval of projection data that is necessary to reconstruct one cross-sectional tomography image, and in this case, may be referred to as 'one cycle angular section of projection data'. For example, one cycle in half-reconstruction is equal to or greater than 180° and one cycle in full reconstruction is 360°.

FIGS. 5A and 5B are views for explaining a scan mode and a scan method used in tomography imaging. In detail, FIG. 5A is a view for explaining tomography imaging according to an axial scan method. Also, FIG. 5A is a view for explaining tomography imaging according to a prospective mode. FIG. 5B is a view for explaining tomography imaging according to a helical scan method. Also, FIG. 5B is a view for explaining tomography imaging according to a retrospective mode.

A scan mode may vary according to whether a cardiac cycle of a patient to be imaged is constant or not. Also, electrocardiogram (ECG) gating may be used to obtain raw data that is used to reconstruct an image. FIGS. 5A and 5B will be explained on the assumption that tomography imaging is performed as the table 105 (see FIG. 3) moves in an axial direction of a patient 505.

Referring to FIG. 5A, the axial scan method is a tomography imaging method involving performing imaging by emitting X-rays when the table 105 is stopped, moving the table 105 by a predetermined interval between 501 and 502, and acquiring raw data by emitting X-rays for a predetermined interval 522. The tomography apparatuses 600 and 700 according to exemplary embodiments may obtain at least one of a first image, a second image, and a target image by performing tomography imaging by using the axial scan method.

Also, referring to FIG. 5A, when a cardiac cycle of the patient 505 is constant, an ECG signal 510 is regularly gated by using the prospective mode. In the prospective mode, a predetermined interval 521 at a time t3 that is separated by a predetermined time from an R peak 511 is automatically selected. Raw data is acquired by applying X-rays to an object for the detected predetermined interval 521. The predetermined interval 522 at a time t4 that is separated by a predetermined time from a next R peak 512 is automatically selected. In this case, imaging is performed by emitting X-rays when the table 105 is stopped, the table 105 is moved again by the predetermined interval between 501 and 502, and then raw data is acquired by emitting X-rays for the predetermined interval 522. A method of performing imaging through movement in an axial direction of the object by predetermined intervals as in FIG. 5A is referred to as an axial half-reconstruction method, and the axial half-reconstruction method may be applied to the tomography apparatuses 600 and 700 according to exemplary embodiments.

Also, a data acquirer 710 reconstructs tomography images 531 and 532 by using the raw data that is acquired in the detected intervals 521 and 522.

Referring to FIG. 5B, the helical scan method is a tomography imaging method involving performing imaging by continuously emitting X-rays while moving the table 105 (see FIG. 3) for a predetermined period of time from t=0 to t=end. In detail, imaging is performed by continuously moving the table 105, on which the patient 505 including the object is placed, for a predetermined period of time at a predetermined speed and continuously emitting X-rays to the object while the table 105 is moved. Accordingly, a movement trajectory 550 of an X-ray source has a helical shape.

Also, referring to FIG. 5B, when a cardiac cycle of the patient 505 who is, for example, an arrhythmia patient, is not constant, the cardiac cycle is not regular and thus may not be detected at one time as in a prospective mode. In this case, an ECG signal 560 is irregularly gated in the retrospective mode. In the retrospective mode, raw data is acquired by emitting X-rays to the object in all cycles of the ECG signal 560 or predetermined continuous cycles, and then partial cycles 561, 562, and 563 for reconstructing a tomography image are selected. That is, in the retrospective mode, a user individually sets the partial cycles 561, 562, and 563 that are to be used to reconstruct an image, detects the partial cycles 561, 562, and 563, and uses raw data acquired in the detected partial cycles 561, 562, and 563 to reconstruct a tomography image.

In detail, in the retrospective mode, imaging is performed by continuously emitting X-rays for a predetermined period of time from t=0 to t=end. Also, tomography imaging may be performed by continuously moving the table 105 for a predetermined period of time, and in this case, the movement trajectory 550 of the X-ray source has a helical shape. A method of performing imaging by continuously emitting X-rays while moving the table 105 as in FIG. 5B is referred to as a helical half-reconstruction method, and the helical half-reconstruction method may be applied to the tomography apparatuses 600 and 700 according to exemplary embodiments.

In detail, when a cardiac cycle of a patient is not constant, tomography imaging may be performed by applying the retrospective mode to the helical scan method. Also, when a cardiac cycle of a patient is constant, tomography imaging may be performed by applying the prospective mode to the axial scan method. However, the present exemplary embodiment is not limited thereto, and tomography imaging may be performed by applying the prospective mode to the helical scan method or tomography imaging may be performed by applying the retrospective mode to the axial scan method.

FIG. 6 is a block diagram of the tomography apparatus 600 according to an exemplary embodiment.

Referring to FIG. 6, the tomography apparatus 600 according to an exemplary embodiment includes a data acquirer 610 and an image reconstructor 620.

The tomography apparatus 600 may be included in the CT system 100 of FIGS. 3 and 4. Also, the tomography apparatus 600 may be included in the medical apparatus 136 or the portable device 138 of FIGS. 5A and 5B and may operate by being connected to the CT system 100. In detail, the tomography apparatus 600 may be any medical imaging apparatus that reconstructs an image by using data acquired by using rays that pass through an object. That is, the tomography apparatus 600 may be any medical imaging apparatus that reconstructs an image by using projection data acquired by using the rays that pass through the object. In detail, the tomography apparatus 600 may be a CT apparatus, an OCT apparatus, or a PET-CT apparatus. Accordingly, a tomography image acquired by the tomography apparatus 600 according to an exemplary embodiment may be a CT image, an OCT image, or a PET image.

The following will be explained on the assumption that a tomography image is a CT image. Also, when the tomography apparatus 600 is included in the CT system 100 of FIGS. 1A and 1B, the data acquirer 610 and the image reconstructor 620 of FIG. 6 may be respectively included in the DAS 116 and the image processing unit 126 of FIG. 3.

The data acquirer 610 acquires tomography data when X-rays are emitted as a cone beam to an object while rotating by one cycle angular section that is less than one rotation. The cone beam is any beam that is radiated into a fan shape.

In detail, the data acquirer 610 may include the X-ray detector 108 and the DAS 116 of FIG. 3 and may obtain tomography data by itself. That is, when the tomography apparatus 600 corresponds to the CT system 100 of FIG. 3, the data acquirer 610 may correspond to the gantry 102 or the DAS 116 that is included in the gantry 102.

The tomography data refers to raw data acquired by tomography imaging performed on the object. The raw data may be projection data acquired by emitting radiation to the object or a sinogram that is a set of projection data. Also, the tomography data may be an image generated by performing filtered back-projection on the projection data or the sinogram.

The following will be explained on the assumption that the tomography data includes a plurality of pieces of projection data corresponding to a plurality of views that are included in the one cycle angular section. Also, the following will be explained on the assumption that the tomography data acquired by one rotation is used to reconstruct multi-slice images.

In detail, when the cone beam is emitted to the object while rotating by the one cycle angular section, the data acquirer 610 acquires the tomography data that is used to reconstruct the multi-slice images corresponding to the plurality of slices. Accordingly, the data acquirer 610 may obtain the tomography data for reconstructing a tomography image corresponding to the plurality of slices through one rotation.

The image reconstructor 620 reconstructs the tomography image by using corrected tomography data acquired by applying a weight to the tomography data. The weight is set based on at least one of a view that is included in the one cycle angular section and a cone angle in the cone beam. The view refers to a point of view from which or a direction in which the X-ray generator 106 views the object when the X-ray generator 106 emits X-rays to the object. The projection data refers to tomography data acquired to correspond to one view and the sinogram refers to tomography data acquired by sequentially arranging a plurality of pieces of projection data corresponding to a plurality of continuous views. The weight will be explained below in detail with reference to FIGS. 12 through 14.

The following will be explained on the assumption that the X-ray generator 106 generates the cone beam that is emitted into a fan shape.

In detail, the image reconstructor 620 compensates for artifacts that occur due to a difference between data in a first view that is included in the one cycle angular section and data in a second view that faces the first view from among the tomography data by using the weight that is set based on at least one of the cone angle and the view. The artifacts compensated for by the image reconstructor 620 will be explained below in detail with reference to FIGS. 10A through 11B.

The following will be explained on the assumption that the data acquirer 610 and the image reconstructor 620 obtain tomography data and reconstruct a tomography image according to a half-reconstruction method.

FIG. 7 is a block diagram of the tomography apparatus 700 according to another exemplary embodiment. In FIG. 7, the data acquirer 710 and an image reconstructor 720 respectively correspond to the data acquirer 610 and the image reconstructor 620 of FIG. 6, and thus a repeated explanation thereof will not be given.

Referring to FIG. 7, the tomography apparatus 700 includes the data acquirer 710 and the image reconstructor 720. Also, the tomography apparatus 700 may further include at least one of a gantry 730, a display unit 740, a user interface unit 750, a storage unit 760, and a communication unit 770. The gantry 730, the display unit 740, the user interface unit 750, the storage unit 760, and the communication unit 770 that are included in the tomography apparatus 700 are respectively the same in terms of operations and configurations to the gantry 102, the display unit 130, the input unit 128, the storage unit 124, and the communication unit 132 of the CT system 100 of FIG. 3, and thus a repeated explanation thereof will not be given.

The data acquirer 710 acquires tomography data when X-rays are emitted as a cone beam to an object while rotating by one cycle angular section that is less than one rotation.

The image reconstructor 720 reconstructs a tomography image by using corrected tomography data acquired by applying a weight to the tomography data.

The gantry 730 includes the X-ray generator 106 (see FIG. 3), the X-ray detector 108 (see FIG. 3), and the DAS 116 (see FIG. 3). The gantry 730 emits X-rays to the object, detects the X-rays that pass through the object, and generates raw data that is tomography data corresponding to the detected X-rays.

In detail, the X-ray generator 106 generates X-rays. The X-ray generator 106 emits the X-rays to the object while rotating about the object. The X-ray detector 108 detects the X-rays that pass through the object. The DAS 116 generates tomography data corresponding to the detected X-rays.

The following will be explained on the assumption that the X-ray generator 106 acquires tomography data by rotating by an interval that is equal to or greater than a half-turn and less than one turn by using a half-reconstruction method.

The X-ray detector 108 may include a 1D detector array (not shown) or a 2D detector array (not shown). When the X-ray detector 108 reconstructs 'one tomography image' by using tomography data acquired by rotating by one cycle angular section, the 'one tomography image' may be a 2D tomography image or a 3D tomography image. The 3D tomography image may be reconstructed by using a plurality of 2D tomography images.

For example, when the X-ray detector 108 includes a 1D detector array and acquires tomography data by rotating by one cycle angular section, one 2D tomography image corresponding to one slice may be generated. In this case, the X-ray detector 108 may generate a plurality of 2D tomography images corresponding to a plurality of slices by using the tomography data acquired by rotating a plurality of times. Also, the X-ray detector 108 may obtain a 3D tomography image by using the plurality of 2D tomography images.

Alternatively, when the X-ray detector 108 includes a 2D detector array and acquires tomography data by rotating by one cycle angular section, multi-slice images corresponding to a plurality of slices may be generated. Each of a plurality of slice images that are included in the multi-slice images may be a 2D tomography image, and a 3D tomography image may be generated by using the plurality of slice images. In this case, the X-ray detector 108 may generate a 3D tomography image by using tomography data acquired by rotating one time.

Also, the image reconstructor 720 may reconstruct a tomography image based on the tomography data. That is, the image reconstructor 720 may generate a tomography image by performing filtered back-projection on original tomography data to which the weight is not yet applied. The tomography image acquired by performing the filtered back-projection on the original tomography data to which the weight is not yet applied is referred to as a 'non-corrected tomography image'.

The display unit 740 displays a predetermined screen. In detail, the display unit 740 may display a user interface screen that is necessary to perform tomography imaging or a reconstructed tomography imaging. Also, the display unit 740 may display information indicating the weight that is used to reconstruct an image and a user interface screen for setting the weight.

Also, the display unit 740 may display a screen including the non-corrected tomography image and the tomography image that is acquired by using the weight.

The user interface unit 750 generates and outputs a user interface screen for receiving a predetermined command or data from a user, and receives the predetermined command or data from the user through the user interface screen. The user interface screen is output by the user interface unit 750 to the display unit 740. The display unit 740 may display the user interface screen. The user may recognize predetermined information on the user interface screen displayed on the display unit 740, and may input the predetermined command or data.

For example, the user interface unit 750 may include a mouse, a keyboard, or an input device including hard keys for inputting predetermined data. For example, the user may input a predetermined command or data by manipulating at least one of the mouse, the keyboard, and the input device included in the user interface unit 750.

Also, the user interface unit 750 may include a touch pad (not shown). In detail, the user interface unit 750 includes the touch pad that is coupled to a display panel (not shown) included in the display unit 740, and outputs a user interface screen on the display panel. When a predetermined command is input through the user interface screen, the touch pad may detect the predetermined command and the user may recognize the predetermined command.

In detail, when the user interface unit 750 includes the touch pad and the user touches a point of the user interface screen, the user interface unit 750 detects the touched point. The user interface unit 750 may transmit information about the detected point to the image reconstructor 720. The image reconstructor 720 may recognize the user's request or command corresponding to a menu displayed on the detected point, may reflect the recognized request or command, and may reconstruct a tomography image.

The storage unit 760 may store data acquired according to tomography imaging. In detail, the storage unit 760 may store at least one of projection data and a sinogram that are tomography data. Also, the storage unit 760 may store various pieces of data and programs that are necessary to reconstruct a tomography image, and may store a finally reconstructed tomography image. Also, the storage unit 760 may store various pieces of data that are necessary to obtain first information and the obtained first information.

Also, the storage unit 760 may include at least one storage medium selected from a flash memory-type storage medium, a hard disk-type storage medium, a multimedia card micro-type storage medium, a card-type memory (e.g., an SD memory or an XD memory), RAM, SRAM, ROM, EEPROM, PROM, a magnetic memory, a magnetic disc, and an optical disc.

The communication unit 770 may communicate with an external device, an external medical apparatus, or the like. For example, the communication unit 770 may be connected to an external CT system or an external tomography apparatus, and may receive tomography data. In this case, the data acquirer 710 may receive the tomography data transmitted through the communication unit 770.

The tomography apparatuses 600 and 700 according to exemplary embodiments may reconstruct an image by using a half-reconstruction method. Also, the tomography apparatuses 600 and 700 according to exemplary embodiments may obtain tomography data by using various scan modes of FIGS. 5A and 5B. Also, the tomography apparatuses 600 and 700 according to exemplary embodiments may perform tomography imaging by using any of an axial scan method and a helical scan method. Also, the tomography apparatuses 600 and 700 may use the X-ray generator 106 that generates a cone beam having a fan shape.

FIGS. 8A and 8B are views for explaining reconstruction of a tomography image according to half-reconstruction. The tomography apparatuses 600 and 700 reconstruct an image by using tomography data acquired by rotating by an interval that is less than one rotation.

In detail, the data acquirer 610 may obtain tomography data that is raw data by performing tomography imaging by rotating about an object by an interval that is less than one rotation. Alternatively, the data acquirer 610 may receive tomography data that is raw data from the outside by performing tomography imaging by rotating about the object by an interval that is less than one rotation.

FIG. 8A is a view for explaining rotation of the X-ray generator 106. FIG. 8B is a view for explaining one cycle angular section in half-reconstruction.

When the X-ray generator 106 emits a cone beam into a fan shape from a predetermined point, in half-reconstruction, the X-ray generator 10 may perform tomography imaging by rotating by an angular section that is equal to or greater than 180° and less than 360° and may reconstruct a tomography image by using raw data acquired in the angular section that is equal to or greater than 180° and less than 360°.

FIG. 8A and subsequent drawings will be explained on the assumption that one cycle angular section is 180+a°. A remaining angle other than 180° in one cycle angular section in a half-reconstruction method is referred to as an 'additional angle'. When one cycle angular section is 180+a° as described above, an additional angle may be a°.

Referring to FIG. 8A, when the X-ray generator 106 emits X-rays to an object 805 from a beam position 810, the X-ray detector 108 detects the X-rays on a detection plane 820. The beam position 810 rotates about the object 805 by 180+a° that is one cycle angular section. Also, the detection plane 820 rotates to correspond to the beam position 810. In detail, the beam position 810 moves by 180° from a +Y-axis to a° Y-axis, and further additionally moves by a° to reach a point 833.

In a half-reconstruction method, one tomography image is reconstructed by using pieces of projection data acquired in a first a° interval 835, a middle angular section 837, and a last a° interval 836.

Referring to FIG. 8B, 180+a° obtained by summing 180° 860, a/2° 873, and a/2° 874 about the object 805 is referred to as one cycle angular section 850. Also, a specific value of a fan angle a° may vary depending on a specification of the X-ray generator 106 or a CT system, and may range from about 50° to about 90°.

In detail, a first angular section 871 and a second angular section 872 that are angular sections included in the one cycle angular section 850 may be conjugate angular sections that face each other. An angle difference between the first angular section 871 and the second angular section 872 that are conjugate angular sections is 180°.

In detail, the first angular section 871 may be a start interval of the one cycle angular section 850 and the second angular section 872 may be an end interval of the one cycle angular section 850, as shown in FIG. 8B.

Since the first angular section 871 and the second angular section 872 are conjugate angular sections and thus views in the first angular section 871 and the second angular section 872 are the same, a surface of the object 805 that is detected when the object 805 is imaged in the first angular section 871 is the same as a surface of the object 805 that is detected when the object 805 is imaged in the second angular section 872. Also, two pieces of tomography data acquired in the two views having an interval of 180° are the same.

That is, the pieces of tomography data acquired in the first angular section 871 and the second angular section 872 contribute to imaging of the same area of the object 805. Accordingly, theoretically, the tomography data acquired in the first angular section 871 has to be the same as the tomography data acquired in the second angular section 872. However, due to characteristics of the cone beam radiated to have a fan shape, the tomography data acquired in the first angular section 871 may be different from the tomography data acquired in the second angular section 872 that faces the first angular section 871. Also, due to the difference between the tomography data acquired in the first angular section 871 and the tomography data acquired in the second angular section 872 that has an angle difference of 180° from the first angular section 871, artifacts occur in a reconstructed tomography image. As described above, the artifacts that occur in the reconstructed tomography image due to the characteristics of the cone beam are referred to as partial scan artifacts. The artifacts that occur due to the characteristics of the cone beam are also referred to as a cone beam effect. Partial scan artifacts will be explained below in detail with reference to FIGS. 10A through 11B.

Also, the following will be explained on the assumption that a tomography apparatus according to an exemplary embodiment is the tomography apparatus 700 of FIG. 7.

FIG. 9 is a view for explaining a beam of X-rays emitted to an object.

When the X-ray generator 106 emits a cone beam while rotating about an object that moves, the data acquirer 710 acquires raw data corresponding to the cone beam.

Referring to FIG. 9, when the X-ray generator 106 emits X-rays from a predetermined position 920 while moving along a trajectory 910 having a circular or helical shape, the X-rays are emitted as a cone beam 930 to an object (not shown). The object may be located on a z-axis.

The X-ray detector 108 detects the X-rays that pass through the object. The X-ray detector 108 may include a 2D detector array 950 having a 2D planar shape, as shown in FIG. 9. The 2D detector array 950 may include a plurality of detector devices that are arranged in a lattice fashion. For example, a plurality of detector devices may be arranged in a vertical column 970 and a plurality of detector devices may be arranged in a horizontal row 960. For example, 128 detector devices may be arranged in the horizontal row 960 and 1000 detector devices may be arranged in the vertical column 970, and thus the 2D detector array 950 may include 128*1000 detector devices.

When the data acquirer 710 acquires tomography data detected by the 2D detector array 950, the image reconstructor 720 may generate a plurality of slice images by using the tomography data acquired by rotating by one cycle angular section. The number of acquired slice images may vary depending on at least one of an interval between slices, a thickness of each slice, and the number of detector devices arranged in the horizontal row 960 of the 2D detector array 950. For example, when 128 detector devices are arranged in the horizontal row 960 and a width of each detector device is 0.5 mm, an interval between slices may be set to 0.5 mm and 128 slice images may be reconstructed. Alternatively, when 128 detector devices are arranged in the horizontal row 960 and a width of each detector device is 0.5 mm, an interval between slices may be set to 1 mm and 64 slice images may be reconstructed. When a plurality of slice images are reconstructed by using tomography data acquired through rotation by one cycle angular section, the plurality of slice images may be referred to as multi-slice images and the 2D detector array 950 may be referred to as a multi-slice detector.

Also, the X-ray detector 108 may include a 1D detector array (not shown). In the 1D detector array, one detector device may be disposed in the horizontal row 960. The 1D detector array may generate only a single slice image by using tomography data acquired through one rotation.

The following will be explained on the assumption that a plurality of slice images are generated by using tomography data acquired by using the 2D detector array 950. When a value of a cone angle is 0°, that is, when an angle between an emitted beam and a detection plane is a right angle (90°), a small number of partial scan artifacts occur in a slice image. As an absolute value of the cone angle increases, the partial scan artifacts that occur in the slice image increase.

Partial scan artifacts that may occur in a single slice image that is generated by using a 1D detector array and multi-slice images that are generated by using a 2D detector array will now be explained below in detail with reference to FIGS. 10A through 11B.

FIGS. 10A and 10B are views for explaining an operation of performing tomography imaging by emitting a cone beam to an object.

In detail, FIG. 10A is a view for explaining partial scan artifacts that occur in a single slice image. FIG. 10B is a view for explaining partial scan artifacts that occur in multi-slice images.

FIG. 10A illustrates cross-sections 1031 and 1032 of a 1D detector array that is included in the X-ray detector 108.

Referring to FIG. 10A, the X-ray generator 106 emits X-rays to an object 1010 while moving along a trajectory 1025. When the X-ray generator 106 emits X-rays to the object 1010 from a first position 1021, the X-rat detector 108 that is located at a second position 1031 facing the first position 1021 detects the X-rays that pass through the object 1010. When the X-ray generator 106 emits X-rays to the object 1010 from a third position 1022, the X-ray detector 108 that is located at a fourth position 1032 facing the third position 1022 detects the X-rays that pass through the object 1010.

A view corresponding to the first position 1021 differs from a view corresponding to the third position 1022 by 180°. Accordingly, tomography data acquired by emitting X-rays from the first position 1021 and tomography data acquired by emitting X-rays from the third position 1022 have to image the same plane or the same area of the object 1010.

Referring to FIG. 10A, both when the x-ray generator 106 that is located at the first position 1021 emits X-rays and when the X-ray generator 106 that is located at the third position 1022 emits X-rays, the X-rays that pass through the object 1010 are detected at the same position by the X-ray detector 108. That is, the same plane or the same area of the object 1010 is imaged from two different facing views in a single slice image.

FIG. 10B illustrates 2D detector arrays 1061 and 1062 that are included in the X-detector 108. The 2D detector arrays 1061 and 1062 each correspond to a cross-section of the horizontal row 960 of the 2D detector array 950 of FIG. 9. Although 128 detector devices are arranged in the horizontal row 960 of the 2D detector array 950 in FIG. 9, FIG. 10B will be explained for convenience on the assumption that the 2D detector arrays 1061 and 1062 that are included in the X-ray detector 108 include 8 detector devices in a horizontal row. Also, the following will be explained on the assumption that the X-ray detector 108 acquires pieces of tomography data corresponding to 8 slice images by using each detector array of 8 detector devices.

Referring to FIG. 10B, the X-ray generator 106 emits X-rays to the object 1010 while moving along the trajectory 1025. In FIG. 10B, when the X-ray generator 106 emits X-rays to the object 1010 from a first position 1051, the 2D detector array 1061 that is located at a second position facing the first position 1051 detects the X-rays that pass through the object 1010. When the X-ray generator 106 emits X-rays to the object 1010 from a third position 1052, the detector array 1062 that is located at a fourth position facing the third position 1052 detects the X-rays that pass through the object 1010.

A view corresponding to the first position 1051 differs from a view corresponding to the third position 1052 by 180°. Accordingly, tomography data acquired by emitting X-rays from the first position 1021 and tomography data acquired by emitting X-rays from the third position 1022 have to image the same plane or the same area of the object 1010.

Referring to FIG. 10B, when the X-ray generator 106 that is located at the first position 1051 emits X-rays, the X-rays that pass through a predetermined area 1070 of the object 1010 are detected in a first column 1072 of the 2D detector array 1061. However, when the X-ray generator 106 that is located at the third position 1052 emits X-rays, the X-rays that pass through the predetermined area 1070 of the object 1010 are detected in a middle portion 1071 between a first column and a second column of the 2D detector array 1062. That is, X-rays emitted from two views that are different from each other by 180°, that is, a view corresponding to the first position 1051 and a view corresponding to the third position 1052, are detected at different planes of the 2D detector arrays 1061 and 1062.

Pieces of tomography data acquired in the first columns 1072 of the 2D detector arrays 1061 and 1062 and used to generate a first slice image corresponding to the first columns 1072 of the 2D detector arrays 1061 and 1062 have to have the same data value in a view corresponding to the first position 1051 and a view corresponding to the third position 1052. However, tomography data for imaging the predetermined area 1070 of the object 1010 in the view corresponding to the first position 1051 and tomography data for imaging the predetermined area 1070 of the object 1010 in the view corresponding to the third position 1052 are obtained by different detector columns.

As described above, a difference between pieces of tomography data acquired in two facing views causes partial scan artifacts.

Also, referring to FIG. 10B, when the X-ray generator 106 is located at the first position 1051, a cone angle refers to an angle at which a cone beam is radiated along a straight line 1091 corresponding to a linear distance between the 2D detector array 1061 and the first position 1051 at which the X-ray generator 106 is located. In detail, a cone angle in a first slice image corresponding to the first column 1072 of the 2D detector array 1061 is a first angle 1092, a cone angle in a second slice image corresponding to the second column 1073 of the 2D detector array 1061 is a second angle 1093, and a cone angle in a third slice image corresponding to a third column 1074 of the 2D detector array 1061 is a third angle 1094. That is, an absolute value of a cone angle increases away from the center of the 2D detector array 1061 toward both ends of the 2D detector array 1061.

Also, a cone angle corresponding to a positive (+) z-axis direction from a reference point 1095 has a positive value and a cone angle corresponding to a negative (−) z-axis direction 1097 from the reference point 1095 has a negative value.

More partial scan artifacts occur in slice images corresponding to outer columns (e.g., 1, 2, 7, and 8 columns) of the 2D detector array 1061 than in slice images corresponding to central columns (e.g., 3, 4, 5, and 6 columns) of the 2D detector array 1061.

FIGS. 11A and 11B are views for explaining partial scan artifacts that occur in a reconstructed tomography image.

FIG. 11A is a view of partial scan artifacts that occur in a reconstructed tomography image according to an exemplary embodiment. FIG. 11B is a view of partial scan artifacts that occur in a reconstructed tomography image according to another exemplary embodiment.

Referring to FIG. 11A, partial scan artifacts that are shaded in specific directions 1120, 1122, and 1123 occur in a reconstructed tomography image 1110.

Also, referring to FIG. 11B, partial scan artifacts that are shaded in specific directions 1160 and 1161 occur in a reconstructed tomography image 1150.

Shading directions and the number of partial scan artifacts vary according to a view or a cone angle. Especially, more partial scan artifacts occur when a 2D detector array corresponds to more multi-slices.

FIG. 12 is a view for explaining a weight used in tomography image reconstruction according to an exemplary embodiment.

Referring to FIG. 12, the X-axis represents a cone angle and the Y-axis represents an angle value or a view value of one cycle angular section. Also, the Z-axis represents a weight.

The weight is set based on at least one of the cone angle and the view value of the one cycle angular section. In detail, the weight is a value applied to tomography data that is acquired by one rotation in order to compensate for artifacts that occur due to a difference between data in a first view included in the one cycle angular section and data in a second view facing the first view. In detail, in order to compensate for the difference between the pieces of data, the image reconstructor 720 may obtain corrected tomography data by applying the weight to tomography data corresponding to at least one view that is included in the one cycle angular section. That is, the image reconstructor 720 may compensate for partial scan artifacts that occur in a reconstructed tomography image described with reference to FIGS. 10A through 11B by using the weight.

In detail, the image reconstructor 720 may set the weight so that as the cone angle increases and as the weight corresponds to the view value farther away from the center of the one cycle angular section, the weight decreases. That is, the weight may be set based on a view and the cone angle, and may have a value that decreases as the view value increases and the cone angle increases.

Alternatively, the weight may be set based on the view, and may have a value that decreases to correspond to the view value away from the center of the one cycle angular section.

Alternatively, the weight may be set based on the cone angle, and may have a value that decreases as the cone angle increases.

FIG. 12 will be explained on the assumption that the weight is set as a value based on both the cone angle and the view value, and thus depends on both the cone angle and the view value. Also, FIG. 12 will be explained on the assumption that a maximum value of the weight is 1 and the one cycle angular section has a value of 180+a°. Also, an upper limit of the cone angle C may be 45° and a lower limit of the cone angle C may be −45°. The following will be explained on the assumption that the cone angle has a value ranging from −45° to 45°.

Referring to FIG. 12, when the cone angle is 0° on the Y-axis, the weight is symmetric. That is, when the cone angle has the same absolute value, the same weight is set. In detail, the weight may be symmetric with respect to a y-z plane. Also, a positive cone angle corresponds to a cone angle corresponding to a positive (+) z-axis direction 1096 of FIG. 10B, and a negative cone angle corresponds to a cone angle corresponding to a negative (−) z-axis direction 1097 of FIG. 10B.

Referring to FIG. 12, a view interval that has a value of 1 that is a maximum weight in the one cycle angular section decreases as an absolute value of the cone angle increases. Also, at a predetermined cone angle, the weight maintains the value of 1 that is a maximum value in a predetermined angular section from a center 1220 of the one cycle angular section and decreases in intervals outside the predetermined angular section as a view is away from the center 1220.

The weight that depends on both the cone angle and the view value has a shape as represented in a graph 1210 of FIG. 12. A specific value of the weight may be optimized and set through experiments and may be set. Also, a user may set a detailed shape of the graph 1210 and a specific value of the weight by using a user interface screen for setting the weight output through the user interface unit 750.

Also, the weight may be proportional to a degree to which projection data acquired in the view and the cone angle contributes to imaging of an object. That is, as a value of the weight increases, a degree to which the projection data acquired in the view and the cone angle contributes to imaging of the object increases, and as a value of the weight decreases, a degree to which the projection data acquired in the view and the cone angle contributes to imaging of the object decreases.

The weight is individually applied to tomography data according to each view and slice. The weight applied to the tomography data according to each view and slice will now be explained in detail with reference to FIGS. 13A through 13C.

FIGS. 13A through 13C are views for explaining a weight used in tomography image reconstruction according to another exemplary embodiment. In detail, FIG. 13A illustrates a weight graph 1310 representing a weight when an absolute value of a cone angle is a highest value. FIG. 13B illustrates a weight graph 1320 representing a weight when an absolute value of a cone angle is a middle value. FIG. 13C illustrates a weight graph 1330 representing a weight when an absolute value of a cone angle is a lowest value.

Also, in the weight graphs 1310, 1320, and 1330 of FIGS. 13A through 13C, the X-axis represents one cycle angular section or a view value that is included in the one cycle angular section, and the Y-axis represents a weight.

The weight may be set to a value that is inversely proportional to a difference between data in a first view that is included in the one cycle angular section and data in a second view facing the first view, in tomography data corresponding to a predetermined cone angle. In detail, when a difference between tomography data acquired in the first view and tomography data acquired in the second view increases, the weight may be set to decrease. When the difference between the tomography data acquired in the first view and the tomography data acquired in the second view decreases, the weight may be set to increase.

As described with reference to FIG. 10B, a data difference between the tomography data acquired in the first view and the tomography data acquired in the second view, in the tomography data acquired in order to reconstruct a slice image, increases as the cone angle increases. Hence, the weight may be set based on a position of a slice of a detector array corresponding to the cone angle. In detail, the weight that is to be applied to pieces of tomography data corresponding to the one cycle angular section, for example, pieces of projection data acquired in the one cycle angular section, may vary according to the cone angle.

Accordingly, in order to compensate for partials can artifacts that occur due to a data difference between facing views, when imaging an object, the image reconstructor 720 reduces the effect of pieces of tomography data acquired in the facing view intervals with the data difference therebetween by using the weight.

The weight is a value directly applied to tomography data. In detail, the weight is a value directly applied to tomography data in order to obtain corrected tomography data having a value that is proportional to or depends on the weight.

In detail, the weight is a value by which tomography data is multiplied, and the image reconstructor 720 may obtain corrected tomography data by multiplying the tomography data by the weight. Also, the image reconstructor 720 may use any of various other calculations than multiplication as long as corrected tomography data having a value that is proportional to or depends on the weight may be acquired.

In detail, in a half-reconstruction method, the weight applied to pieces of tomography data acquired in both end intervals of the one cycle angular section may be reduced. Accordingly, a value of corrected tomography data acquired by multiplying the reduced weight by the tomography data is reduced to be less than a value of the tomography data, and a degree to which the corrected tomography data contributes to imaging of the object is also reduced.

Referring to FIG. 13A, the weight graph 1310 represents a weight on a y-z plane when an absolute value of a cone angle of the graph 1210 of FIG. 12 is C.

Referring to FIG. 13A, when the absolute value of the cone angle is C that is a maximum value, a difference between data in a first view that is included in the one cycle angular section and data in a second view that faces the first view is the highest.

Referring to FIG. 13B, the weight graph 1320 represents a weight on the y-z plane when an absolute value of the cone angle of the graph 1210 of FIG. 12 is C/2.

Referring to FIG. 13B, when the absolute value of the cone angle is C/2, a difference between data in the first view that is included in the one cycle angular section and data in the second view that faces the first view is less than that when the absolute value of the cone angle is C.

Referring to FIG. 13C, the weight graph 1330 represents a weight on the y-z plane when an absolute value of the cone angle of the graph 1210 of FIG. 12 is 0 that is a minimum value.

Referring to FIG. 13C, when the absolute value of the cone angle is 0, a difference between data in the first view that is included in the one cycle angular section and data in the second view that faces the first view is less than that when the absolute value of the cone angle is C/2. Also, in an entire cone angular section, a difference between data in the first view that is included in the one cycle angular section and data in the second view that faces the first view is the lowest when the absolute value of the cone angle is 0.

Accordingly, referring to FIGS. 13A, 13B, and 13C, in a graph representing a weight, when an absolute value of a cone angle is C that is a maximum value, an angular section or a view interval in which the weight has a maximum value in the weight graph 1310 has a minimum value. In a graph representing a weight, when an absolute value of a cone angle is 0 that is a minimum value, an angular section or a view interval in which the weight has a maximum value in the weight graph 1330 has a maximum value.

In detail, when an absolute value of a cone angle is C that is a maximum value and a view value in the weight graph 1310 is a1, a weight is 1. When the view value is equal to or less than a1, the weight is reduced to be proportional to the view value. Also, although the weight and the view value are in a linear relationship when the view value is equal to or less than a1 in FIG. 13A, the weight and the view value may have a relationship other than the linear relationship as long as the weight and the view value are proportional to each other.

When an absolute value of a cone angle is C/2 that is a middle value and a view value in the weight graph 1320 is a3, a weight is 1. When the view value is equal to or less than a3, the weight is reduced to be proportional to the view value. Also, although the weight and the view value are in a linear relationship when the view value is equal to or less than a3 in FIG. 13B, the weight and the view value may have a relationship other than the linear relationship as long as the weight and the view value are proportional to each other.

When an absolute value of a cone angle is 0 that is a minimum value and a view value in the weight graph 1330 is a5, a weight is 1. When the view value is equal to or less than a5, the weight is reduced to be proportional to the view value. Also, although the weight and the view value are in a linear relationship when the view value is equal to or less than a5 in FIG. 13C, the weight and the view value may have a relationship other than the linear relationship as long as the weight and the view angle are proportional to each other.

The values a1, a3, and a5 satisfy a1>a3>a5.

Also, referring to FIGS. 13A, 13B, and 13C, a weight graph representing a weight corresponding to a predetermined cone angle is symmetric with respect to a center C 1311 in a 180+a° interval of one cycle angular section.

Also, tomography data acquired in the one cycle angular section at a predetermined cone angle corresponding to a predetermined slice includes pieces of projection data acquired in a plurality of views included in an angular section from 0° to 180+a°. Accordingly, corrected tomography data is acquired by multiplying a weight by projection data according to each view.

Also, referring to FIG. 13B, the image reconstructor 720 acquires corrected projection data corresponding to a view of a4 by multiplying a weight of 0.5 by projection data acquired when an absolute value of a cone angle is C/2 and the view is a/4. The image reconstructor 720 acquires corrected projection data corresponding to a view of a2 by multiplying a weight of 0.8 by projection data acquired when an absolute value of a cone angle is C/2 and the view is a/2. The image reconstructor 720 acquires corrected projection data corresponding to a view of a3 by multiplying a weight of 1 by projection data acquired when an absolute value of a cone angle is c/2 and the view is a3. Corrected tomography data includes pieces of corrected projection data acquired in all views included in the one cycle angular section according to a plurality of slices.

The image reconstructor 720 may reconstruct a tomography image by performing filtered back-projection on the corrected tomography data acquired by applying the weight to the tomography data. Alternatively, the image reconstructor 720 may reconstruct a tomography image by performing back-projection on the corrected tomography data acquired by applying the weight to the tomography data.

In detail, when tomography data includes a plurality of pieces of projection data corresponding to a plurality of views included in the one cycle angular section, the image reconstructor 720 may reconstruct a tomography image by performing back-projection or filtered back-projection on a plurality of pieces of corrected projection data acquired by applying the weight to each of the plurality of pieces of projection data corresponding to the one cycle angular section.

An operation of reconstructing a tomography image by performing filtered back-projection will be explained below in detail with reference to FIGS. 15A and 15B.

Also, the image reconstructor 720 reconstructs a tomography image according to each slice. In detail, the image reconstructor 720 sets a weight for a predetermined slice corresponding to a predetermined cone angle. The weight set for the predetermined slice may include a plurality of weight values corresponding to a plurality of views included in the one cycle angular section, and may be set as in the graphs of FIGS. 12 through 13C.

A tomography image corresponding to a predetermined slice is acquired by using a weight according to the predetermined slice.

Since the image reconstructor 720 reconstructs a tomography image by applying a weight that is individually set for each predetermined slice to tomography data, noise characteristics of tomography images according to a plurality of slices included in multi-slice images may be different from one another.

FIGS. 14A and 14B are views for explaining a weight used in tomography image reconstruction according to another exemplary embodiment.

In detail, FIG. 14A is a view for explaining an operation of acquiring tomography data through rotation about an object 1401 by 180+a° that is one cycle angular section when an absolute value of a cone angle is 0 that is a minimum value. FIG. 14B is a view for explaining an operation of acquiring tomography data through about the object 1401 by 180+a° that is the one cycle angular section when an absolute value of a cone angle is c=45° that is a maximum value.

Referring to FIG. 14A, the X-ray generator 106 emits X-rays to the object 1401 while rotating along a trajectory 1410, and a 2D detector array (not shown) that is included in the X-ray detector 108 detects the X-rays that pass through the object 1401. The data acquirer 710 acquires a plurality of pieces of projection data corresponding to a plurality of views that are included in one cycle angular section 1405. A curve 1450 is a reference line indicating a degree to which projection data acquired in each view contributes to imaging of the object 1401. In detail, an interval between the trajectory 1410 and the curve 1450 may indicate a degree to which projection data acquired in each view contributes to imaging of the object 1401.

In detail, an interval between the trajectory 1410 and the curve 1450 in a view of a5 1441 is a maximum interval and an interval between the trajectory 1410 and the curve 1450 in a view of (180+a°)−a5 1446 is a maximum interval. Also, an interval between the trajectory 1410 and the curve 1450 in an interval from the view of a5 1441 to the view of (180+a°)−a5 1446 is a maximum interval. Hence, all of projection data from projection data acquired in the view of a5 1441 to projection data acquired in the view of (180+a°)−a5 1446 completely contributes to imaging of the object 1401. However, a degree to which pieces of projection data acquired in a plurality of views included in an angular section 1461 before the view of a5 1441 and an angular section 1462 after the view of (180+a°)−a5 1446 contribute to imaging of the object 1401 is reduced.

In detail, partial scan artifacts in the angular section 1461 before the view of a5 1441 and in the angular section 1462 after the view of (180+a°)−a5 1446 are increased. Accordingly, the image reconstructor 720 may adaptively reduce partial scan artifacts by reducing a degree to which pieces of projection data acquired in the angular section 1461 before the view of a5 1441 and in the angular section 1462 after the view of (180+a°)−a5 1446 contribute to imaging of the object 1401.

Referring to FIG. 14B, the X-ray generator 106 emits X-rays to the object 1401 while rotating along the trajectory 1410, and a 2D detector array (not shown) that is included in the X-ray detector 108 detects the X-rays that pass through the object 1401. The data acquirer 710 acquires a plurality of pieces of projection data corresponding to a plurality of views included in the one cycle angular section 1405. A curve 1420 is a reference line indicating a degree to which projection data acquired in each view contributes to imaging of the object 1401. In detail, an interval between the trajectory 1410 and the curve 1420 may indicate a degree to which projection data acquired in each view contributes to imaging of the object 1401.

In detail, an interval 1422 between the trajectory 1410 and the curve 1420 in a view of a1 1421 is a maximum interval and an interval 1424 between the trajectory 1410 and the curve 1420 in a view of (180+a°)−a1 1423 is a maximum interval. An interval between the trajectory 1410 and the curve 1420 in an interval from the view of a1 1421 to the view of (180+a°)−a1 1423 is a maximum interval. Hence, all of projection data from projection data acquired in the view of a1 1421 to projection data acquired in the view of (180+a°)−a1 1423 completely contributes to imaging of the object 1401. However, a degree to which pieces of projection data acquired in a plurality of views included in an angular section 1431 before the view of a1 1421 and an angular section 1432 after the view of (180+a°)−a1 1423 contribute to imaging of the object 1401 is reduced.

In detail, partial scan artifacts in the angular section 1431 before the view of a1 1421 and the angular section 1432 after the view of (180+a°)−a1 1423 are increased. Accordingly, the image reconstructor 720 may adaptively reduce partial scan artifacts by reducing a degree to which pieces of projection data acquired in the angular section 1431 before the view of a1 1421 and the angular section 1432 after the view of (180+a°)−a1 1423 contribute to imaging of the object 1401.

FIGS. 15A and 15B are views for explaining an operation of reconstructing a tomography image according to an exemplary embodiment. In detail, FIGS. 15A and 15B are views for explaining an operation of the image reconstructor 720 for reconstructing a slice image corresponding to a predetermined cone angle.

In detail, FIG. 15A is a weight graph representing a weight applied to a predetermined cone angle. FIG. 15B is a view for explaining an operation of acquiring projection data in one cycle angular section in order to reconstruct a slice image corresponding to a predetermined cone angle.

FIG. 15A illustrates a weight graph 1590 that is applied to tomography data for reconstructing a slice image corresponding to a cone angle when an absolute value of the cone angle is 20. Also, the X-axis represents one cycle angular section or a view value that is included in the one cycle angular section, and the Y-axis represents a weight.

In detail, in the weight graph 1590, the weight has a 1 value that is a maximum value in a view interval from 60° to 210° and has a value less than 1 in other intervals.

Referring to FIG. 15B, the X-ray generator 106 performs tomography imaging by rotating about an object 1501. The object 1501 may include at least one organ and/or tissue therein. FIG. 15B will be explained on the assumption that the object 1501 has a circular shape.

FIG. 15B will be explained on the assumption that the X-ray generator 106 performs tomography imaging by rotating about the object 1501 and reconstructs a tomography image by using filtered back-projection. Also, FIG. 15B will be explained on the assumption that the object 1501 has a circular shape. Also, one cycle angular section is 180+a° in FIGS. 8, 12, and 13 whereas tomography imaging is performed through rotation of 180° in FIG. 15B. In detail, for example, when a=90, one cycle angular section is 270°, in other words, an angular section from 0° to 270°.

FIG. 15B will be explained for convenience on the assumption that the X-ray generator 106 performs tomography imaging by rotating by an interval of 180°, specifically, from a first time T1 to a second time T2 corresponding to an angular section between 45° and 225°.

Referring to FIG. 15B, the X-ray generator 106 emits X-rays to the object 1501 from a plurality of points having predetermined angular sections therebetween while moving along a source trajectory 1510 having a circular shape and acquires projection data. In FIG. 15B, each of the plurality of points that are included in the source trajectory 1510 indicates a view. The data acquirer 710 acquires filtered projection data by filtering the projection data.

In FIG. 15B, a plurality of points on the source trajectory 1510 are the points at which and from which the X-ray generator 106 is located and emits X-rays. Also, in FIG. 5B, each of the plurality of points on the source trajectory 1510 indicates a view. For example, the X-ray generator 106 may emit X-rays to the object 1501 while moving by predetermined angular sections such as 0.5°-intervals, 1°-intervals, or 3°-intervals. The X-ray generator 106 starts to rotate at the first time T1 and rotates until the second time T2. Accordingly, the first time T1 corresponds to a rotation angle of 0° and the second time T2 corresponds to a rotation angle of 180°.

Also, in FIG. 15B, a plurality of objects 1513, 1514, 1515, 1516, and 1517 are objects at a plurality of times, e.g., the first through fifth times T1, T2, T12, T13, and T14, that are included in the one cycle angular section. Also, although each object whose state is constant and that does not move at each of the first through fifth times T1, T2, T12, T13, and T14 is illustrated in FIG. 15B, the object may be a moving object such as the heart or abdomen.

In detail, when the X-ray generator 106 emits X-rays to the object 1501 at the first time T1, the X-rays that are emitted in a direction 1532 pass through the object 1513 and a signal 1531 is obtained. A signal value of the obtained signal 1531 on a surface of the object 1513 may be changed due to a transmittance difference of the X-rays between materials. In detail, a signal value on a surface arranged in parallel to the direction 1532 in which the X-rays are emitted may be changed.

Also, when the X-ray generator 106 emits X-rays to the object 1501 at the third time T12, the X-rays that are emitted in a direction 1534 pass through the object 1514 and a signal 1533 is obtained. A signal value of the obtained signal 1533 on a surface arranged in parallel to the direction 1534 in which the X-rays are emitted may be changed.

Also, when the X-ray generator 106 emits X-rays to the object 1501 at the fourth time T13, the X-rays that are emitted in a direction 1536 pass through the object 1515 and a signal 1535 is obtained. A signal value of the obtained signal 1535 on a surface arranged in parallel to the direction 1536 in which the X-rays are emitted may be changed.

Also, when the X-ray generator 106 emits X-rays to the object 1501 at the fifth time T14, the X-rays that are emitted in a direction 1538 pass through the object 1516 and a signal 1537 is obtained. A signal value of the obtained signal 1537 on a surface arranged in parallel to the direction in which the X-rays are emitted may be changed.

Also, when the X-ray generator 106 emits X-rays to the object 1501 at the second time T2, the X-rays that are emitted in a direction 1524 pass through the object 1517 and a signal 1539 is obtained. A signal value of the obtained signal 1539 on a surface arranged in parallel to the direction in which the X-rays are emitted may be changed.

Also, at the first time T1, since the signal 1531 includes information about the surface arranged in the direction 1532, projection data 1551 acquired by performing filtered back-projection on the signal 1531 contributes to imaging of the surface arranged in the direction 1532. At the third time T12, since the signal 1533 includes information about the surface arranged in the direction 1534, filtered projection data corresponding to the signal 1533 contributes to imaging of the surface arranged in the direction 1534. That is, projection data acquired in each view contributes to imaging of a surface of an object corresponding to each view. This may be explained by using a Fourier slice theorem indicating a relationship between a value of projection data acquired by projecting a parallel beam to the object 1501 and a frequency component of an image. The 'view' corresponds to a direction, a position, and/or a rotation angle in and/or at which the X-ray generator 106 emits X-rays to the object 1501.

Also, the DAS 116 of FIG. 3 may obtain, for example, the signal 1531, and the image processor 126 may process the obtained signal 1531 and may generate filtered projection data. An image is acquired by performing back-projection on the filtered projection data.

Also, the DAS 116 of FIG. 3 may obtain projection data including pixel values based on the signal 1531.

The data acquirer 710 may obtain projection data that is tomography data, and the image reconstructor 720 may obtain corrected projection data that is corrected tomography data by applying a weight to the projection data. In detail, the image reconstructor 720 may obtain the corrected projection data by multiplying the projection data corresponding to a predetermined view by a weight corresponding to the predetermined view.

In detail, at the first time T1, the DAS 116 acquires the projection data 1551 including pixel values indicating an object to be imaged based on the obtained signal 1531. Also, the data acquirer 710 acquires or receives the projection data 1551. Also, referring to FIG. 15A, a weight corresponding to a view of 40° corresponding to the first time T1 is 0.5. Accordingly, the image reconstructor 720 acquires corrected projection data 1561 by multiplying the projection data 1551 by 0.5 that is the weight in the view corresponding to the first time T1. In detail, the image reconstructor 720 acquires the corrected projection data 1561 including pixel values of '0, 1, 1, and 0' by multiplying the projection data 1551 including pixel values of '0, 2, 2, and 0' by the weight of 0.5.

Also, at the third time T12, the DAS 116 acquires projection data 1552 including pixel values indicating an object to be imaged based on the acquired signal 1533. Also, the data acquirer 710 acquires or receives the projection data 1552. Also, referring to FIG. 15A, a weight corresponding to a view of 90° corresponding to the third time T12 is 1. Accordingly, the image reconstructor 720 acquires corrected projection data 1562 by multiplying the projection data 1552 by 1 that is the weight in the view corresponding to the third time T12. In detail, the image reconstructor 720 acquires the corrected projection data 1562 including pixel values of '0, 2, 2, and 0' by multiplying the projection data 1552 including pixel values of '0, 2, 2, and 0' by the weight of 1.

Also, at the fourth time T13, the DAS 116 acquires projection data 1553 including pixel values indicating an object to be imaged based on the obtained signal 1535. Also, the data acquirer 710 acquires or receives the projection data 1553. Also, referring to FIG. 15A, a weight corresponding to a view of 135° corresponding to the fourth time T13 is 1. Accordingly, the image reconstructor 720 acquires corrected projection data 1563 by multiplying the projection data 1553 by the weight of 1 in the view corresponding to the fourth time T13.

Also, at the fifth time T14, the DAS 116 acquires projection data 1554 including pixel values indicating an object to be imaged based on the obtained signal 1537. Also, the data acquirer 710 acquires or receives the projection data 1554. Also, referring to FIG. 15A, a weight corresponding to a view of 180° corresponding to the fourth time T13 is 1. Accordingly, the image reconstructor 720 acquires corrected projection data 1564 by multiplying the projection data 1554 by the weight of 1 in the view corresponding to the fifth time T14.

Also, at the second time T2, the DAS 116 acquires projection data 1556 including pixel values indicating an object to be imaged based on the obtained signal 1539. Also, the data acquirer 710 acquires or receives the projection data 1556. Also, referring to FIG. 15A, a weight corresponding to a view of 230° corresponding to the second time T2 is 0.5. Accordingly, the image reconstructor 720 acquires corrected projection data 1565 by multiplying the projection data 1556 by the weight of 0.5 in the view corresponding to the second time T2.

For convenience of explanation, FIG. 15B has been explained on the assumption that pieces of corrected tomography data corresponding to five views are acquired by applying weights to pieces of tomography data acquired in the five views, that is, the view of 40°, the view of 90°, the view of 135°, the view of 180°, and the view of 230° that are included in one cycle angular section. However, corrected tomography data is acquired by applying weights to all views that are included in the one cycle angular section.

Also, a weight may be set for one view group including several views. For example, when one cycle angular section is 270° and the X-ray generator 106 performs tomography imaging by moving by 1°-intervals, views for which projection data is acquired are a view of 1°, a view of 2°, a view of 3°, . . . , and a view of 270°. In this case, every three views may be grouped, and a first weight may be applied to the view of 1°, the view of 2°, and the view of 3°, a second weight may be applied to the view of 4°, the view of 5°, and the view of 6°, and a third weight may be applied to the view of 7°, the view of 8°, and the view of 9°.

Also, although FIG. 15B has been explained for convenience on the assumption that weights are applied to all pieces of projection data acquired in all views that are included in one cycle angular section, weights may be applied to only pieces of projection data acquired in some views that are included in one cycle angular section. For example, few partial scan artifacts occur in a central interval that is an angular section corresponding to the center of one cycle angular section and many partial scan artifacts occur in boundary intervals that are both side intervals other than the central interval in the one cycle angular section. Hence, pieces of corrected projection data may be acquired by applying weights to only pieces of projection data acquired in the boundary intervals and pieces of projection data acquired in the central interval may be directly used to reconstruct a tomography image without applying weights to the pieces of projection data acquired in the central interval.

Accordingly, in order to compensate for a difference between data in a first view that is included in one cycle angular section and data in a second view that faces the first view from among tomography data, the image reconstructor 720 may obtain corrected tomography data by applying a weight to only tomography data corresponding to at least one view that is included in the one cycle angular section.

As described with reference to FIG. 15B, the image reconstructor 720 acquires pieces of corrected projection data and reconstructs a tomography image by accumulating and back-projecting the acquired pieces of corrected projection data. That is, the image reconstructor 720 may obtain an image of an object by using back-projection that involves projecting projection data to image pixels. In detail, the image reconstructor 720 acquires pieces of filtered corrected projection data by filtering the pieces of corrected projection data and reconstructs a tomography image by accumulating and filtered back-projecting the pieces of filtered corrected projection data.

An operation performed by the image reconstructor 720 to reconstruct a tomography image by performing filtered back-projection will now be explained with reference to FIGS. 16A and 16B.

FIGS. 16A and 16B are views for explaining an operation of reconstructing a tomography image according to another exemplary embodiment.

FIG. 16A is a view for explaining an example where the X-ray generator 106 performs tomography imaging by rotating about the object 1501. Also, FIG. 16B is a view for explaining an operation of performing back-projection on pieces of projection data acquired by filtering raw data acquired through tomography imaging. FIG. 16A is the same as FIG. 15B, and thus a detailed explanation thereof will not be given.

FIGS. 16A and 16B will be explained on the assumption that one cycle angular section is 180°, like in FIG. 15B. Also, in FIG. 16B, a 1 view corresponds to a first time T1 of FIG. 16A and '180° accumulation' refers to accumulation of data acquired during an interval from the first time T1 to a second time T2 of FIG. 16A.

Referring to FIG. 16B, a surface 1652 of the object 1501 at the first time T1 is shown on a back-projection image 1651 corresponding to the first time T1. Pieces of filtered projection data for a plurality of views acquired through counterclockwise rotation are accumulated and back-projected.

For example, a back-projection image 1653 is acquired by accumulating and back-projecting pieces of filtered projection data acquired in an angular section of 22.5°. A partial surface 1654 of the object 1501 is shown on the back-projection image 1653.

Next, a back-projection image 1655 is acquired by accumulating and back-projecting pieces of filtered projection data acquired in an angular section of 45°. A partial surface 1656 of the object 1501 is shown on the back-projection image 1655.

Next, a back-projection image 1657 is acquired by accumulating and back-projecting pieces of filtered projection data acquired in an angular section of 98°. A partial surface 1658 of the object 1501 is shown on the back-projection image 1657.

Next, a back-projection image 1659 is acquired by accumulating and back-projecting pieces of filtered projection data acquired in an angular section of 180°. An entire surface of the objet 1501 is shown on the back-projection image 1659.

In order to obtain a reconstructed image indicating the object 1501, the image reconstructor 720 acquires corrected projection data by multiplying projection data acquired in a predetermined view by a weight corresponding to the predetermined view. Accordingly, the image reconstructor 720 may reduce a degree to which the projection data contributes to imaging of the object 1501 at a cone angle and in a view where partial scan artifacts are increased. That is, the tomography apparatuses 600 and 700 according to exemplary embodiments may effectively reduce partial scan artifacts that occur dependently on at least one of a cone angle and a view, by using a weight.

Also, the tomography apparatuses 600 and 700 according to exemplary embodiments obtain corrected tomography image by applying a weight to tomography data and obtain a tomography image by performing filtered back-projection on the corrected tomography data. Accordingly, without providing an additional apparatus for reducing partial scan artifacts or without performing an additional complex process for removing artifacts, the tomography apparatuses 600 and 700 according to exemplary embodiments may effectively reduce partial scan artifacts. In detail, since the tomography apparatuses 600 and 700 according to exemplary embodiments obtain corrected projection data by applying a weight to projection data acquired in each of a plurality of views that are included in one cycle angular section and obtain a tomography image by performing filtered back-projection on the corrected projection data, a complex filtering operation for removing artifacts is not performed. That is, since an additional filtering operation is not performed and thus characteristics of the acquired projection are not changed, a signal-to-noise ratio (SNR) may be higher than that when artifacts are removed by using an additional filtering operation.

FIG. 17 is a flowchart of a method 1700 of reconstructing a tomography image according to an exemplary embodiment. Operations that are included in the method 1700 are the same as operations of elements that are included in the tomography apparatuses 600 and 700 according to exemplary embodiments. Accordingly, when the method 1700 is explained, the same explanation as that already made with reference to FIGS. 1 through 16 will not be given.

In operation 1710, when X-rays are emitted as a cone beam to an object while rotating by one cycle angular section that is less than one rotation, tomography data is acquired. Operation 1710 may be performed by the data acquirer 710 of the tomography apparatus 700.

The tomography data that is raw data acquired by tomography imaging performed on the object may be projection data acquired by emitting radiation to the object or a sinogram that is a set of projection data. Also, the tomography data may be an image generated by performing filtered back-projection on the projection data or the sinogram.

The following will be explained on the assumption that the tomography data includes a plurality of pieces of projection data corresponding to a plurality of views that are included in the one cycle angular section. Also, the following will be explained on the assumption that the tomography data acquired by one rotation is used to reconstruct multi-slice images.

In operation 1720, a weight is acquired based on at least one of a view that is included in the one cycle angular section and a cone angle in the cone beam. Operation 1720 may be performed by the image reconstructor 720 of the tomography apparatus 700.

In operation 1730, a tomography image is reconstructed by using corrected tomography data acquired by applying the weight acquired in operation 1720 to the tomography data. Operation 1730 may be performed by the image reconstructor of the tomography apparatus 700.

The embodiments of the inventive concept may be written as computer programs and may be implemented in general-use digital computers that execute the programs using a computer-readable recording medium.

Examples of the computer-readable recording medium include magnetic storage media (e.g., ROM, floppy disks, hard disks, etc.), optical recording media (e.g., CD-ROMs, or DVDs), etc.

While one or more embodiments of the inventive concept have been described with reference to the figures, it will be understood by those of ordinary skill in the art that various changes in form and details may be made therein without departing from the spirit and scope of the inventive concept as defined by the following claims. Accordingly, the above embodiments and all aspects thereof are examples only and are not limiting.

The invention claimed is:

1. A tomography apparatus comprising:
    a data acquirer configured to acquire tomography data when X-rays are emitted by an X-ray generator as a cone beam to an object while the X-ray generator rotates by one cycle angular section that is less than one full rotation; and
    an image reconstructor configured to reconstruct a tomography image by using corrected tomography data that is acquired by applying to the tomography data a weight that is set based on a view value included in the one cycle angular section and a cone angle of the cone beam,
    wherein the view value corresponding to a maximum weight decreases as the cone angle increases.

2. The tomography apparatus of claim 1, wherein the image reconstructor compensates for artifacts that occur due to a difference between data in a first view that is included in the one cycle angular section and data in a second view that faces the first view in the tomography data, by using the weight.

3. The tomography apparatus of claim 1, wherein the weight decreases as the view value is farther away from a center of the one cycle angular section.

4. The tomography apparatus of claim 1, wherein the weight decreases as the cone angle increases.

5. The tomography apparatus of claim 1, wherein when a detector array detects X-rays that pass through the object, the weight is set based on a position of a slice of the detector array corresponding to the cone angle.

6. The tomography apparatus of claim 1, wherein when the tomography data comprises a plurality of pieces of projection data corresponding to a plurality of views that are included in the one cycle angular section, the image reconstructor reconstructs the tomography image by performing back-projection or filtered back-projection on a plurality of pieces of corrected projection data that are acquired by applying the weight to each of the plurality of pieces of projection data.

7. The tomography apparatus of claim 1, wherein the image reconstructor sets the weight so that a value of the weight applied to at least one projection data acquired in at least one view corresponding to a central interval of the one cycle angular section is greater than a value of the weight applied to at least one projection data acquired in at least one view corresponding to an interval other than the central interval.

8. The tomography apparatus of claim 1, wherein the image reconstructor reconstructs a plurality of tomography images corresponding to a plurality of slices by using the corrected tomography data, wherein noise characteristics of the plurality of tomography images are different from one another.

9. The tomography apparatus of claim 1, wherein the view value indicates a view from among a plurality of views included in the one cycle angular section.

10. The tomography apparatus of claim 1, wherein the view value specifies a view angle included in the one cycle angular section.

11. The tomography apparatus of claim 1, wherein the image reconstructor further comprises a user interface unit configured to receive from a user an input comprising a detailed shape of a graph and a specific value of the weight using a user interface screen for setting the weight output.

12. The tomography apparatus of claim 1, wherein the image reconstructor is configured such that a filtering operation is not performed and a signal-to-noise ratio is higher than when artifacts are removed by using the filtering operation.

13. A method of reconstructing a tomography image, the method comprising:

when X-rays that are emitted as a cone beam by an X-ray generator to an object while the X-ray generator rotates by one cycle angular section that is less than one full rotation, acquiring tomography data;

acquiring a weight based on a view value included in the one cycle angular section and a cone angle of the cone beam; and reconstructing a tomography image by using corrected tomography data that is acquired by applying the weight to the tomography data, wherein the view value corresponding to a maximum weight decreases as the cone angle increases.

14. The method of claim 13, wherein the reconstructing of the tomography image further comprises reconstructing the tomography image by compensating for artifacts that occur due to a difference between data in a first view that is included in the one cycle angular section and data in a second view that faces the first view in the tomography data by using the weight.

15. The method of claim 13, wherein the weight decreases as the view value is farther away from a center of the one cycle angular section.

16. The method of claim 13, wherein the weight decreases as the cone angle increases.

17. The method of claim 13, wherein when a detector array detects X-rays that pass through the object, the weight is set based on a position of a slice of the detector array corresponding to the cone angle.

18. The method of claim 13, wherein the reconstructing of the tomography image comprises, when the tomography data comprises a plurality of pieces of projection data corresponding to a plurality of views that are included in the one cycle angular section, reconstructing the tomography image by performing back-projection or filtered back-projection on a plurality of pieces of corrected projection data that are acquired by applying the weight, which is set according to each of the plurality of views, to each of the plurality of pieces of projection data.

19. The method of claim 13, wherein the acquiring of the weight comprises setting the weight so that a value of the weight applied to at least one projection data acquired in at least one view corresponding to a central interval of the one cycle angular section is greater than a value of the weight applied to at least one projection data acquired in at least one view corresponding to a interval other than the central interval.

20. The method of claim 13, wherein the reconstructing of the tomography image comprises receiving an input from a user on a user interface unit comprising a detailed shape of a graph and a specific value of the weight.

* * * * *